US00RE44417E

(19) United States
(12) Reissued Patent
Bartish, Jr. et al.

(10) Patent Number: US RE44,417 E
(45) Date of Reissued Patent: Aug. 6, 2013

(54) BANANA CAGE

(75) Inventors: Charles M. Bartish, Jr., Providence, RI (US); Douglas Bireley, Barrington, RI (US); Bradley Moore, West Vancouver (CA)

(73) Assignee: DePuy Spine, Inc., Raynham, MA (US)

(21) Appl. No.: 13/037,597

(22) Filed: Mar. 1, 2011

Related U.S. Patent Documents

Reissue of:
(64) Patent No.: 7,500,991
Issued: Mar. 10, 2009
Appl. No.: 10/334,599
Filed: Dec. 31, 2002

(51) Int. Cl.
*A61F 2/44* (2006.01)

(52) U.S. Cl.
USPC ..... 623/17.11; 623/17.16

(58) Field of Classification Search
USPC ..... 623/17.11–17.16; 606/86 A, 279
See application file for complete search history.

(56) References Cited

U.S. PATENT DOCUMENTS

| | | | | |
|---|---|---|---|---|
| 4,743,256 | A | 5/1988 | Brantigan | |
| 4,904,261 | A | 2/1990 | Dove et al. | |
| 5,192,327 | A | 3/1993 | Brantigan | |
| 5,865,845 | A | 2/1999 | Thalgott | |
| 6,080,158 | A * | 6/2000 | Lin | 606/247 |
| 6,143,032 | A | 11/2000 | Schafer et al. | |
| 6,245,108 | B1 | 6/2001 | Biscup | |
| 6,296,664 | B1 | 10/2001 | Middleton | |
| 6,387,130 | B1 | 5/2002 | Stone et al. | |
| 6,482,233 | B1 | 11/2002 | Aebi et al. | |
| 6,579,318 | B2 * | 6/2003 | Varga et al. | 623/17.11 |
| 6,699,288 | B2 | 3/2004 | Moret et al. | |
| 6,712,852 | B1 * | 3/2004 | Chung et al. | 623/17.11 |
| 6,946,000 | B2 * | 9/2005 | Senegas et al. | 623/17.11 |
| 7,060,073 | B2 * | 6/2006 | Frey et al. | 606/85 |
| 7,500,991 | B2 | 3/2009 | Bartish, Jr. et al. | |
| 2002/0022886 | A1 | 2/2002 | Fuss et al. | |
| 2002/0055781 | A1 | 5/2002 | Sazy | |
| 2002/0077700 | A1 | 6/2002 | Varga et al. | |
| 2002/0165612 | A1 | 11/2002 | Gerber et al. | |
| 2003/0083748 | A1 | 5/2003 | Lee et al. | |
| 2003/0100950 | A1 | 5/2003 | Moret | |
| 2003/0139812 | A1 | 7/2003 | Garcia et al. | |
| 2004/0117020 | A1 | 6/2004 | Frey et al. | |
| 2004/0143330 | A1 | 7/2004 | Sazy | |

FOREIGN PATENT DOCUMENTS

| | | | |
|---|---|---|---|
| JP | 11-506658 | A | 6/1999 |
| WO | 01/28469 | A2 | 4/2001 |
| WO | 01/70144 | A1 | 9/2001 |
| WO | 02/17823 | A2 | 3/2002 |
| WO | WO 02/17823 | A1 | 3/2002 |

OTHER PUBLICATIONS

Eurpoean Search Report dated Jun. 5, 2004 EP03258242.
Japanese Office Action for application No. 2003-433182, issued Jan. 20, 2009.

* cited by examiner

*Primary Examiner* — Pedro Philogene
(74) *Attorney, Agent, or Firm* — Nutter McClennen & Fish LLP

(57) ABSTRACT

A banana shaped intevertebral fusion cage having a domed profile, an internal planar wall defining first and second graft chambers, asymmetrically disposed leading and trailing insertion, and an anterior wall recess.

48 Claims, 33 Drawing Sheets

BANANA CAGE

Matter enclosed in heavy brackets [ ] appears in the original patent but forms no part of this reissue specification; matter printed in italics indicates the additions made by reissue.

*This application is a reissue of U.S. Pat. No. 7,500,991.*

BACKGROUND OF THE INVENTION

The leading cause of lower back pain arises from rupture or degeneration of lumbar intervertebral discs. Pain in the lower extremities is caused by the compression of spinal nerve roots by a bulging disc, while lower back pain is caused by collapse of the disc and by the adverse effects of articulation weight through a damaged, unstable vertebral joint. One proposed method of managing these problems is to remove the problematic disc and replace it with a porous device that restores disc height and allows for bone growth therethrough for the fusion of the adjacent vertebrae. These devices are commonly called "fusion devices".

U.S. Pat. No. 4,743,256 ("Brantigan") discloses an improved surgical method for eliminating spinal back pain caused by ruptured or degenerated vertebral discs by spanning the disc space between adjacent vertebrae with rigid fusion devices, or "cages", having surfaces facilitating bone ingrowth and bottomed on prepared sites of the vertebrae to integrate the implant with the vertebrae and to provide a permanent weight supporting strut maintaining the disc space. Brantigan teaches that these cages are linearly inserted into the disc space from the posterior side of the spine.

Because the Brantigan cage is inserted linearly into the disc space from the posterior side of the spine, its upper and lower surfaces bear against only one of the two sides of the opposing vertebral endplates. For this reason, two Brantigan cages must be used in each surgical procedure.

U.S. Pat. No. 6,143,032 ("Schafer") discloses an intervertebral fusion device having a banana-shape, including leading and trailing walls connected by a convex wall and a concave wall. This implant may also have a wedge shape wherein the height of the concave wall is smaller than the height of the convex wall. See col. 3, lines 8-9.

U.S. Pat. No. 6,245,108 ("Biscup") discloses a device comprising a pair of D-shaped cages adapted to fit adjacent one another within the disc space. Each cage has a lordotic anterior-posterior wedge shape, and its curved wall is shorter than its opposite wall so that, in combination, the device provides a dome shape.

U.S. Pat. No. 6,387,130 ("Stone") discloses providing a plurality of implants which when arranged sequentially produce a banana-shaped device which rests on the anterior half of the disc space. Each implant may have a lordotic shape, as in FIG. 5, and the plurality of implants may be tapered for distraction and lordosis, as in FIG. 6.

PCT patent Publication No. WO 01/28469 A2 ("Frey") discloses an intervertebral fusion device having a banana-shape, including leading and trailing walls connected by a convex wall and a concave wall. The Frey cage is inserted non-linearly into the disc space from the posterior side of the spine, so that the leading wall thereof comes to rest on one side of the spine, and the trailing wall comes to rest on the other side of the spine. Because the Frey cage bears against each side of each opposing endplate, only one Frey cage need be used in each surgical procedure.

However, Frey discloses positioning the Frey cage in an essentially lateral orientation about midway between the anterior and posterior ends of the endplates. Because the rim of the endplates provides the most stable bearing surface, the Frey implant must have a width that extends across the width of the endplate. Typically, the width of the such cages is about 32 mm.

In addition, the upper bearing surface of the Frey implant has a single inter-end support 1019 connecting the anterior and posterior walls of the implant. Because there is only a single support, the cage is susceptible to rocking about this single support.

In addition, although Frey discloses a pair of insertion holes at either end of the implant, the geometry of the insertion holes appear to be symmetric about the midline of the cage. Accordingly, this symmetric hole placement does not provide the surgeon with any intra-operative flexibility to adjust for differences in patient anatomy or approach.

In addition, although Frey discloses that the anterior wall can have a height greater than the posterior wall, Frey does not disclose the posterior wall can have a height greater than the anterior wall.

Lastly, although Frey discloses that the upper and lower bearing surfaces can have grooves therein, Frey does not disclose that the upper and lower bearing surfaces can have teeth thereon.

PCT Published patent application No. WO 01/70144 ("Scolio") discloses a banana-shaped implant having three vertically-disposed through holes defining two internal planar walls therebetween. The implant further has a concave wall having a plurality of openings disposed therethrough. Lastly, the implant has a lordotic anterior-posterior wedge, as well as front part 3 to rear part 4 angle. FIG. 7 of Scolio discloses a similar implant having two vertically disposed holes. It appears that the geometry of this cage (lordosis and a medial-lateral slope) requires that it be used to support only one half of the disc space, as with the Brantigan cage.

PCT Published patent application No. WO 02/17823 ("Kim") discloses a banana-shaped implant having two vertically-disposed through-holes defining a single internal planar walls therebetween. The implant further has a concave wall and a convex wall, each having a plurality of openings disposed therethrough. The upper and lower bearing surfaces of the implant have pyramidal teeth disposed thereon. Lastly, the implant has a lordotic anterior-posterior wedge, as well as front part 3 to rear part 4 angle. FIGS. 10A-E disclose placing the implant on the anterior half of the disc space with its convex wall facing anteriorly.

The Kim cage has a single insertion hole, and so does not provide for surgeon flexibility as discussed above. In addition, it has only a single middle strut, thereby raising the possibility of tilting in the medial-lateral direction. Lastly, the requirement that it have a constant polygonal cross-section precludes the possibility of doming.

U.S. Published patent application 2002/0055781("Sazy") discloses a banana-shaped implant having a mesh structure. FIG. 7 of Sazy discloses the implant as positioned essentially in the middle of the disc space.

U.S. Published patent application 2002/0077700 ("Vargas") discloses a banana-shaped non-porous implant. Paragraph 0055 of Vargas teaches to set the implant as far anteriorly in the disc space as possible.

SUMMARY OF THE INVENTION

The present inventors have appreciated that, although the Frey cage may be useful for supporting the middle portion of the disc space, it may be more desirable for a fusion cage to be adapted to support the anterior portion of the disc space. When a device is so positioned, the surgeon using a posterior or posterolateral approach is provided with additional room posterior to the device in which to place graft materials such as autograft. In addition, when the device is so positioned within the anterior third portion of the disc space, the resulting cantilever action upon the vertebral bodies forces a more natural lordotic relation between the vertebral bodies, and also reduces the stresses distributed through the implant.

Likewise, the device is superior to that of Vargas because, although Vargas device is positioned in the anterior portion of the disc space, its lack of openings preclude its filling with graft material.

Therefore, the device of the present invention provides for enhanced filling of the disc space with graft material when compared to these prior art devices.

Accordingly, in accordance with the present invention, there is provided an intervertebral fusion device comprising:

a) an anterior wall having a convex horizontal cross section,
b) a posterior wall,
c) first and second end walls between (and preferably connecting) the anterior and posterior walls
d) an upper bearing surface between the anterior and posterior walls (preferably, having an anterior portion above the anterior wall and a posterior portion above the posterior wall), and at least one upper opening therethrough adapted to promote bony fusion, and
e) a lower bearing surface having an anterior portion below the anterior wall, a posterior portion below the posterior wall, and at least one lower opening therethrough adapted to promote bony fusion, wherein the upper and lower openings are in communication to promote bony fusion through the device, wherein the anterior wall has a middle portion, lateral end portions, each having a maximum height, and the maximum height of the middle portion is greater than the maximum height of the lateral end portions, and wherein the posterior portion of each bearing surface is adapted to bear against the anterior half of the disc space .

DETAILED DESCRIPTION OF THE INVENTION

Figure 1A:
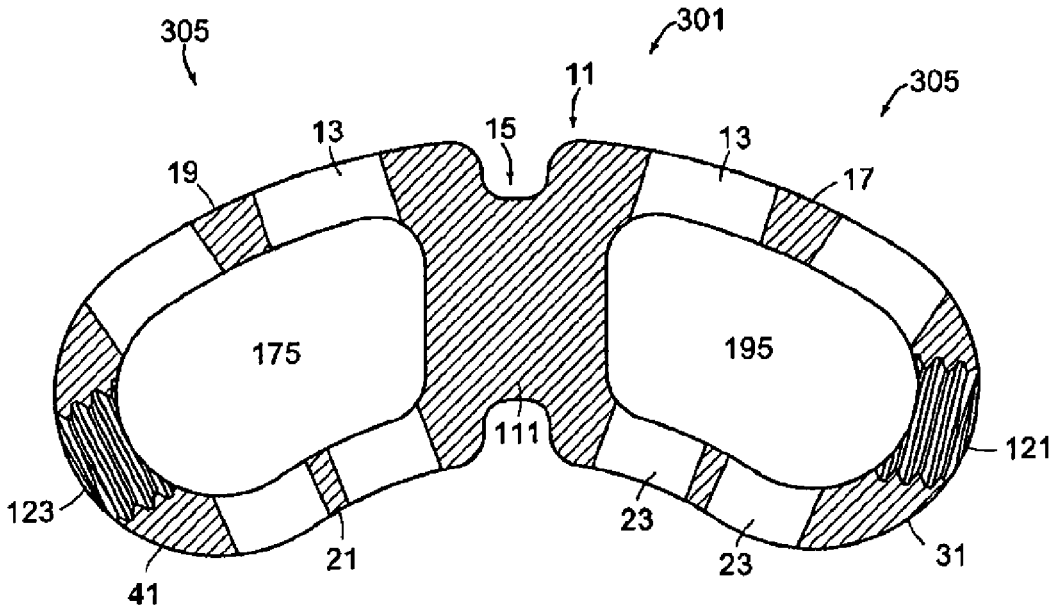
FIGS. 1a-1g disclose various views of a lordotic banana shaped cage of the present invention.
Figure 1B:
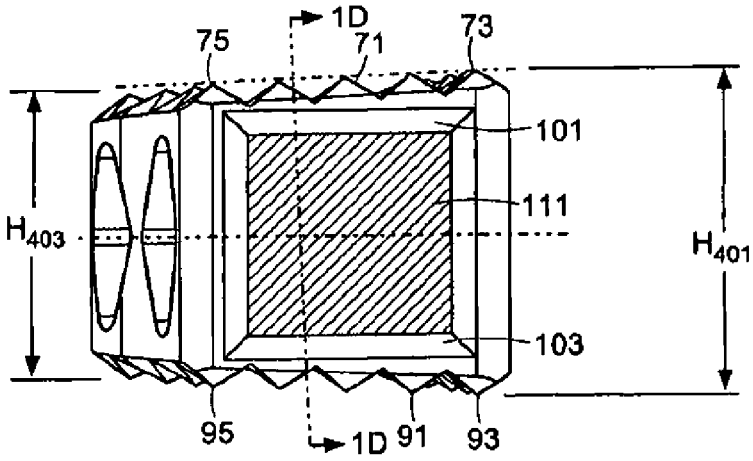
Figure 1C:
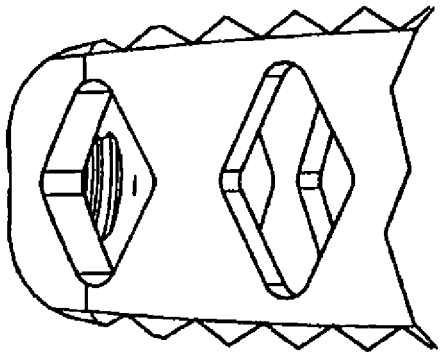

Now referring to FIGS. 1a-1g, there is provided an intervertebral fusion device 1 comprising:

a) an anterior wall 11 having a horizontal cross section having a convex shape,
b) a posterior wall 21 having a horizontal cross section having a concave shape,
c) first 31 and second 41 end walls connecting the anterior and posterior walls
d) an upper bearing surface 71 having an anterior portion 73 above the anterior wall and a posterior portion 75 above the posterior wall, and
e) a lower bearing surface 91 having an anterior portion 93 below the anterior wall and a posterior portion 95 below the posterior wall, wherein the anterior portion of each bearing surface is adapted to bear against the anterior cortical rim, and wherein the posterior portion of each bearing surface is adapted to bear against the anterior aspect of the disc space.

Preferably, this cage is adapted so that the first end wall is first inserted into the disc space, the device is then rotated.

Preferably, the anterior wall is convexly curved. More preferably, it is shaped to conform to the shape of the anterior cortical rim of the vertebral endplates. When the anterior wall is so shaped the cage may rest upon the anterior cortical rim of the vertebral endplates and provide support. Typically, the convex curve of the anterior wall is in the form of an arc having a radius of between 15 mm and 25 mm mm. Such curves allow the cage to be inserted in a non-linear fashion.

In some embodiments, the anterior wall comprises openings 13 adapted to promote bone fusion therethrough.

In some embodiments, these openings have a height and a width, wherein the height of the opening is greater than the width. In this condition, the surrounding material is better able to withstand axial compressive stresses.

In some embodiments, the openings comprises between about 14 areal percent ("areal %") and about 50 areal % of the anterior wall, preferably between 20 areal % and 30 areal %. In contrast to the Frey structure, whose anterior openings comprises roughly about 70 areal % of the anterior wall, these embodiments have more mass and so provide greater strength to the structure than the Frey structure. This enhanced strength is important because the overall size of the device of the present invention is typically smaller than that of the Frey device.

In some embodiments, the horizontal cross section of the anterior wall comprises a recessed portion 15, thereby defining right 17 and left 19 lateral anterior wall end portions. This recess may be used as an alignment guide within the disc space. It may also allow the implant to be pre-bent (material characteristics permitting) prior to insertion. Lastly, it may provide a port for gripping the implant to effect its removal.

Figure 3A:
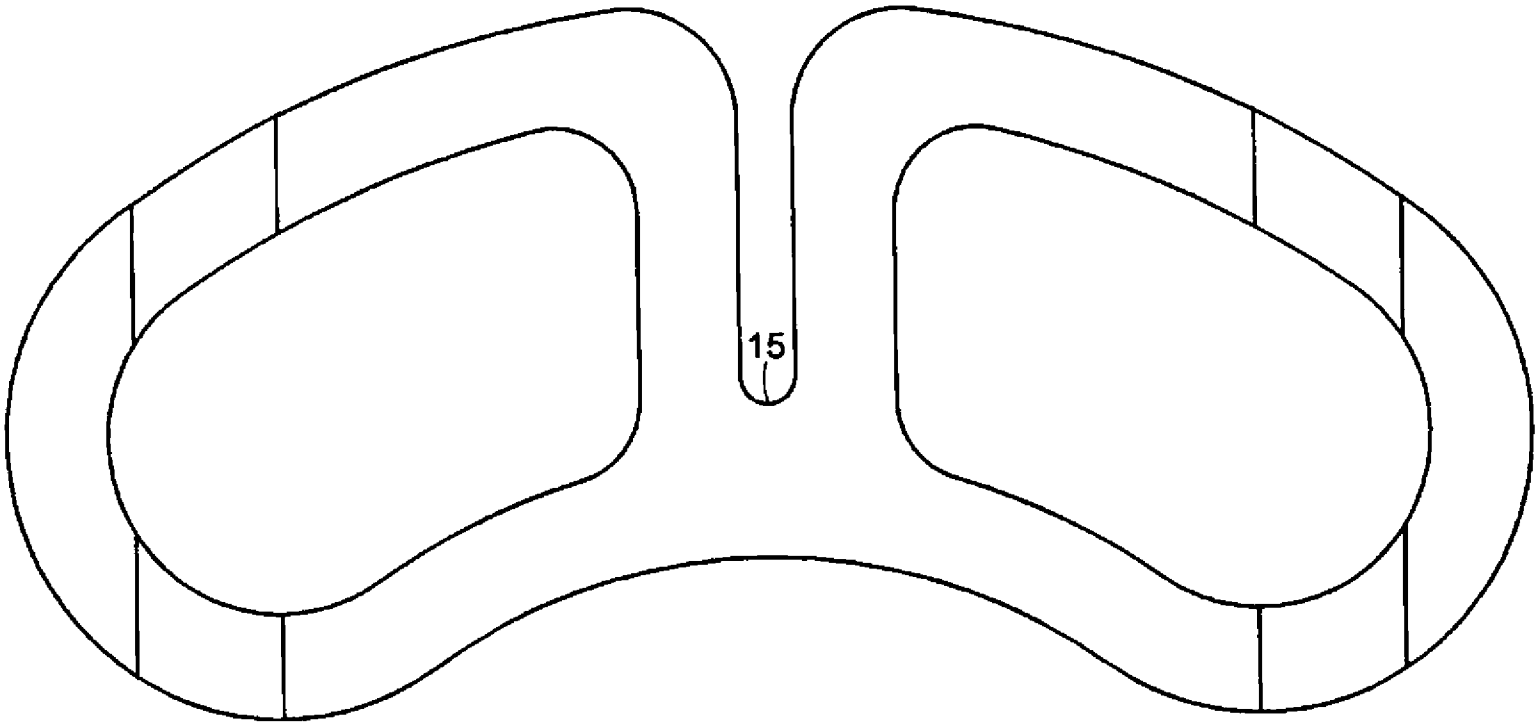
FIGS. 3a-3c disclose various views of a banana shaped cage of the present invention wherein the anterior wall has a recess extending nearly to the posterior wall.
Figure 3B:
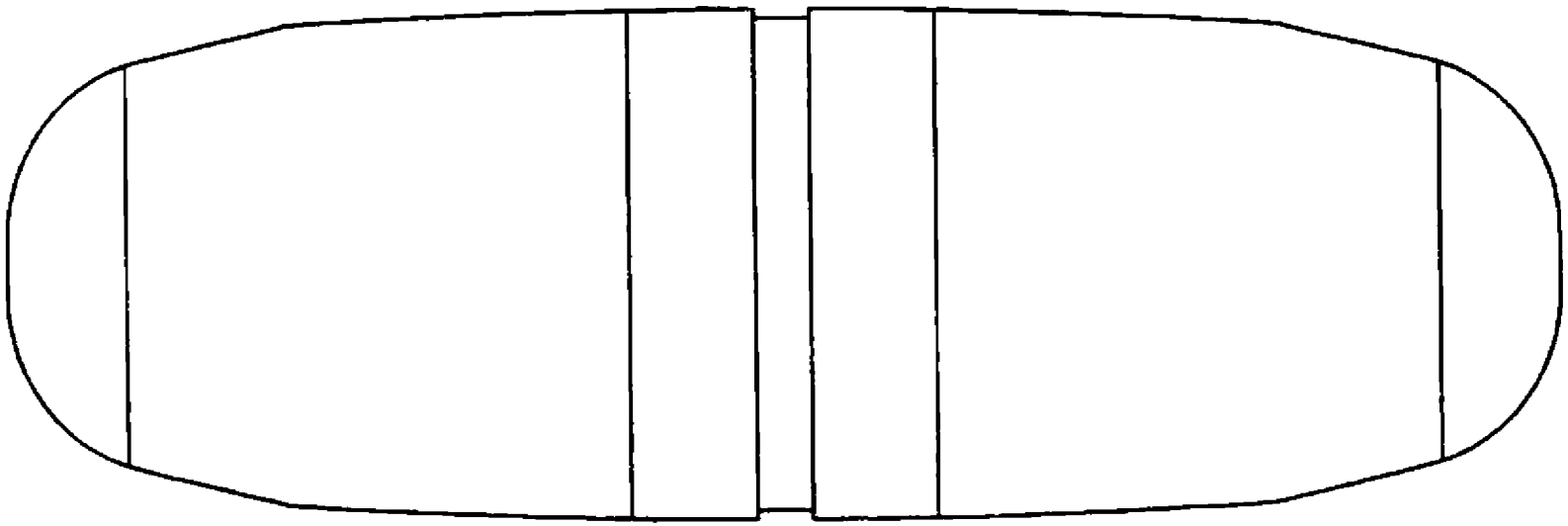
Figure 3C:
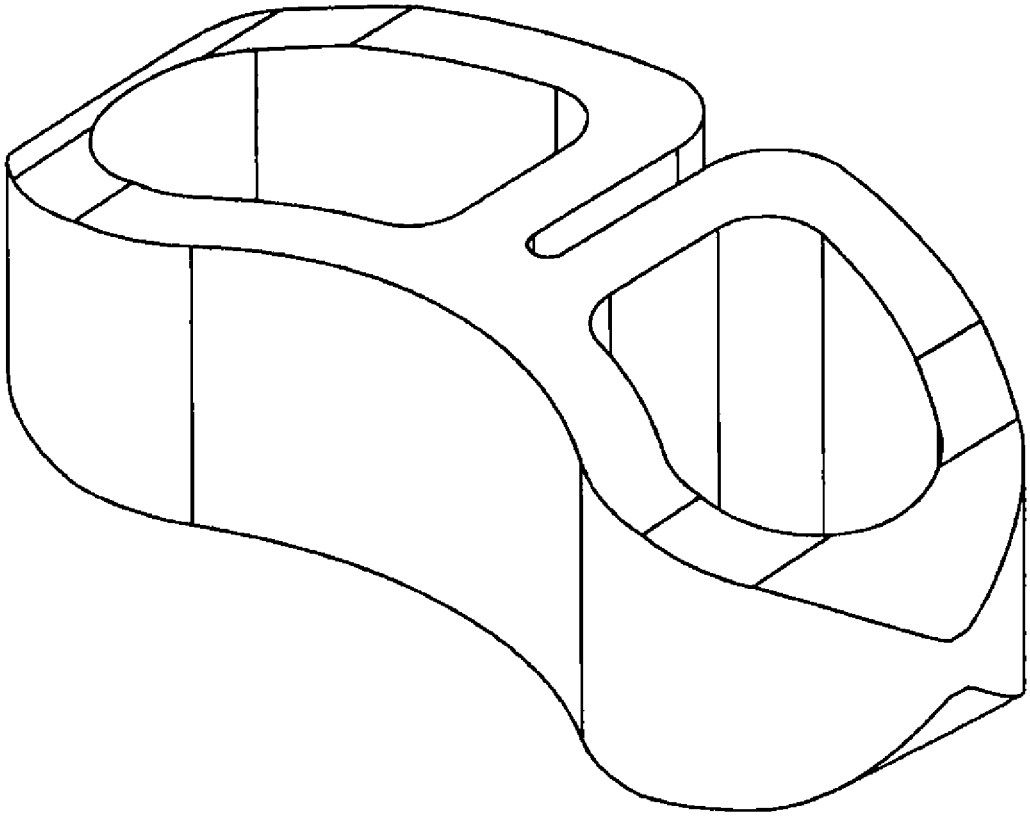

In some embodiments, as in FIG. 3a, the recessed portion of the anterior wall extends more than half way through the width of the cage, and the central posterior notch has been filled with material to create a smooth posterior wall. This embodiment is advantageous because it defines an effective "dual chamber" implant and has more material at the center of the posterior wall than that of the cage of FIGS. 1a-1h, thereby allowing the implant to more effectively resist bending in response to high impaction forces experienced during insertion.

Therefore, in accordance with the present invention, there is provided an intervertebral fusion device comprising:

a) an anterior wall having a horizontal cross section having a convex shape and a recessed portion, b) a posterior wall, c) first and second end walls between (and preferably connecting) connecting the anterior and posterior walls d) an upper bearing surface between the anterior and posterior walls (and preferably having an anterior portion above the anterior wall and a posterior portion above the posterior wall), and at least one upper opening therethrough adapted to promote bony fusion, and e) a lower bearing surface having an anterior portion below the anterior wall, a posterior portion below the posterior wall, and at least one lower opening therethrough adapted to promote bony fusion.

In embodiments particularly advantageous in the lumbar spine, the range of the maximum height of the anterior wall is between about 5 mm and 18 mm, and the range of the maximum thickness of the anterior wall is between about 1 mm and 3 mm.

Preferably, the posterior wall is concave curved. Such curves allow the cage to be inserted in a non-linear fashion. Typically, the concave curve of the posterior wall is in the form of an arc having a radius of between 5 mm and 20 mm.

In some embodiments, the posterior wall comprises openings 23 adapted to promote bone fusion therethrough.

Figure 1D:
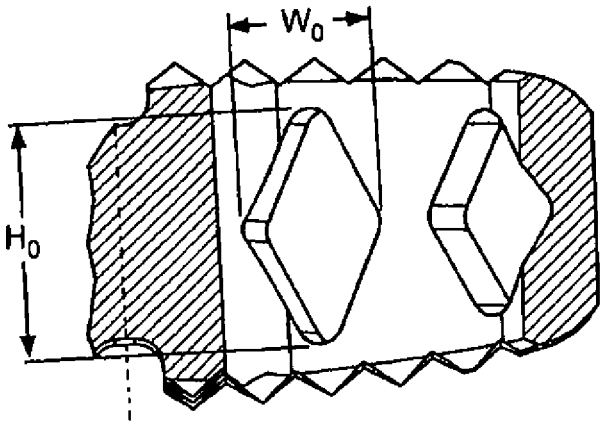
Figure 1F:
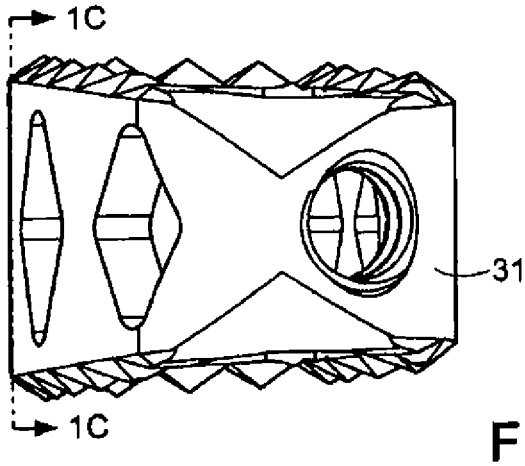
Figure 1E:
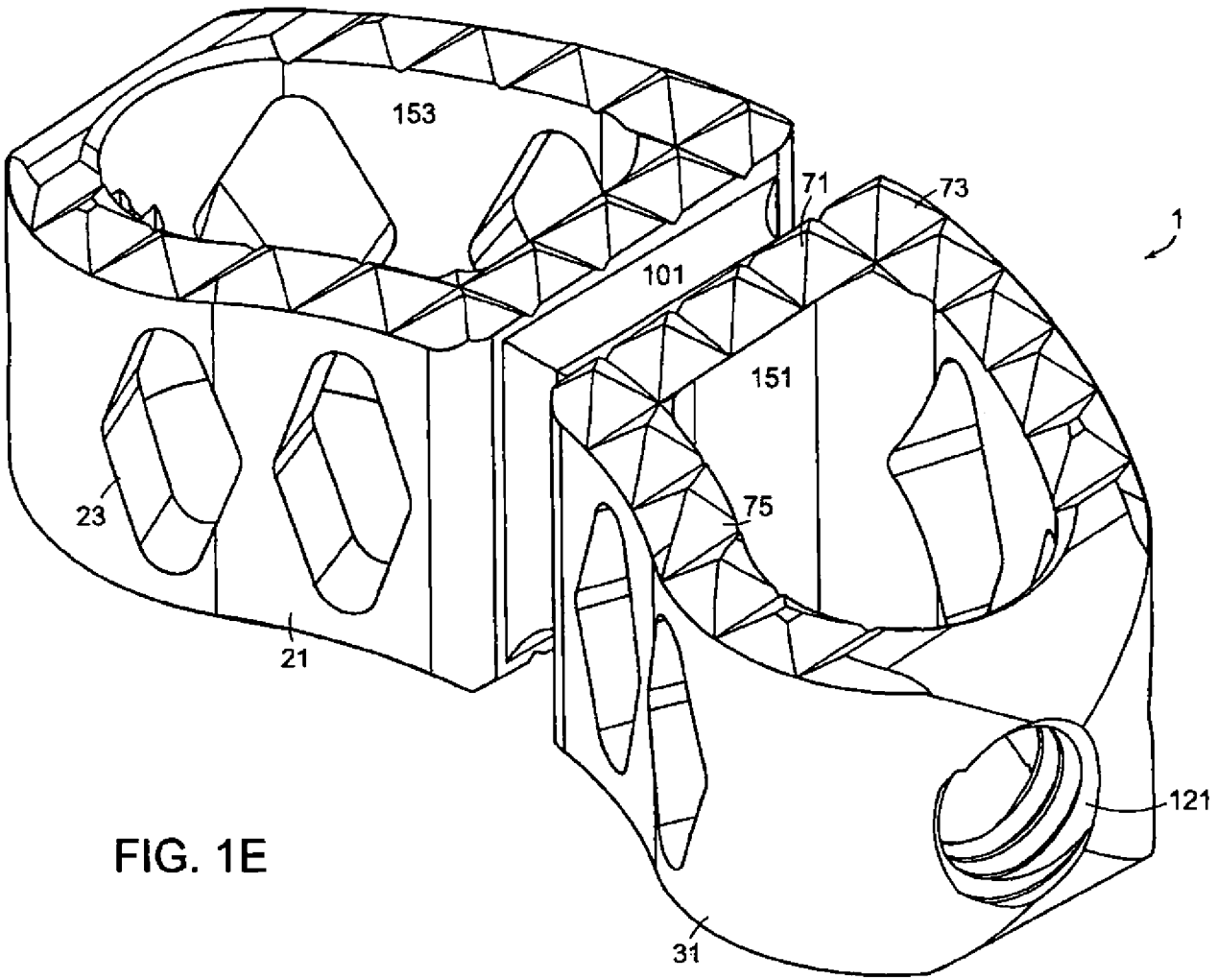
Figure 1G:
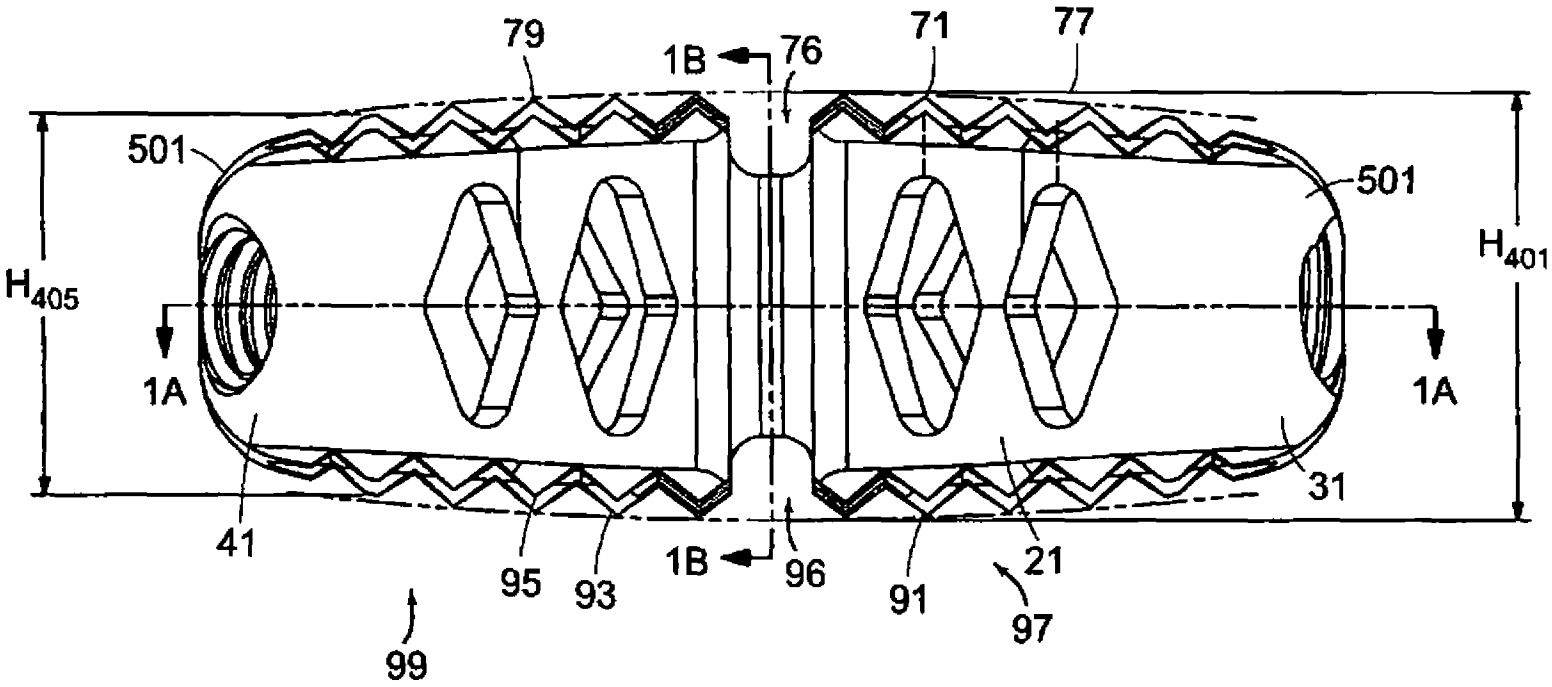

In some embodiments, as in FIG. 1d, these openings have a height $H_O$ and a width $W_O$, wherein the height of the opening is greater than the width. In this condition, the surrounding material is better able to withstand axial compressive stresses.

In some embodiments, the openings in the posterior wall in combination comprise between about 14 areal % and about 50 areal % of the anterior wall, preferably between 20 areal % and 30 areal %. In this range, the openings are large enough to allow nutrient transfer through the wall. In contrast to the Frey structure, whose posterior openings comprise about 70 areal % of the posterior wall, these embodiments have more mass and so provide greater strength to the structure than the Frey structure. This enhanced strength is important because the overall size of the device of the present invention is typically smaller than that of the Frey device.

Figure 5A:
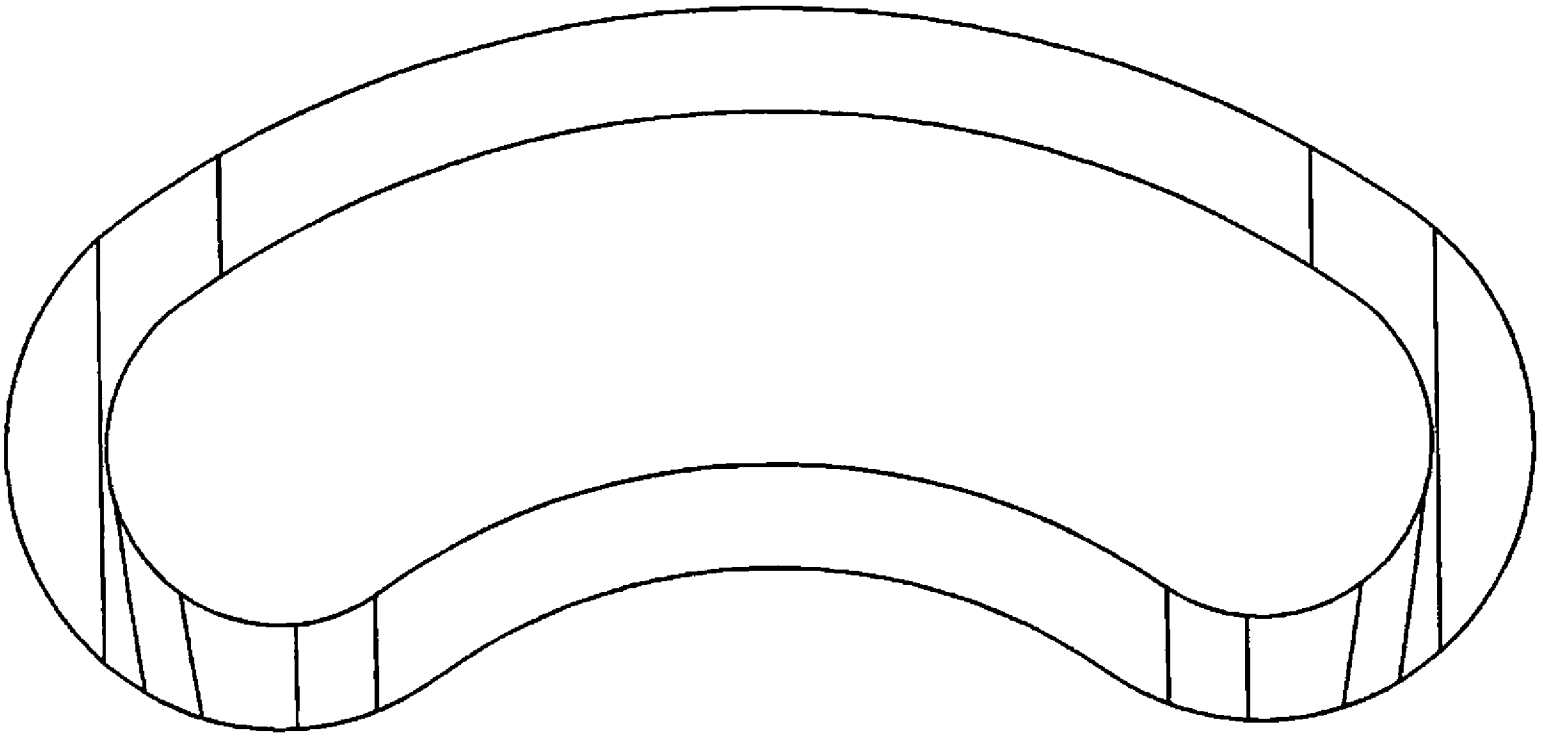
FIGS. 5a-5c disclose various views of another lordotic banana shaped cage of the present invention.
Figure 5B:
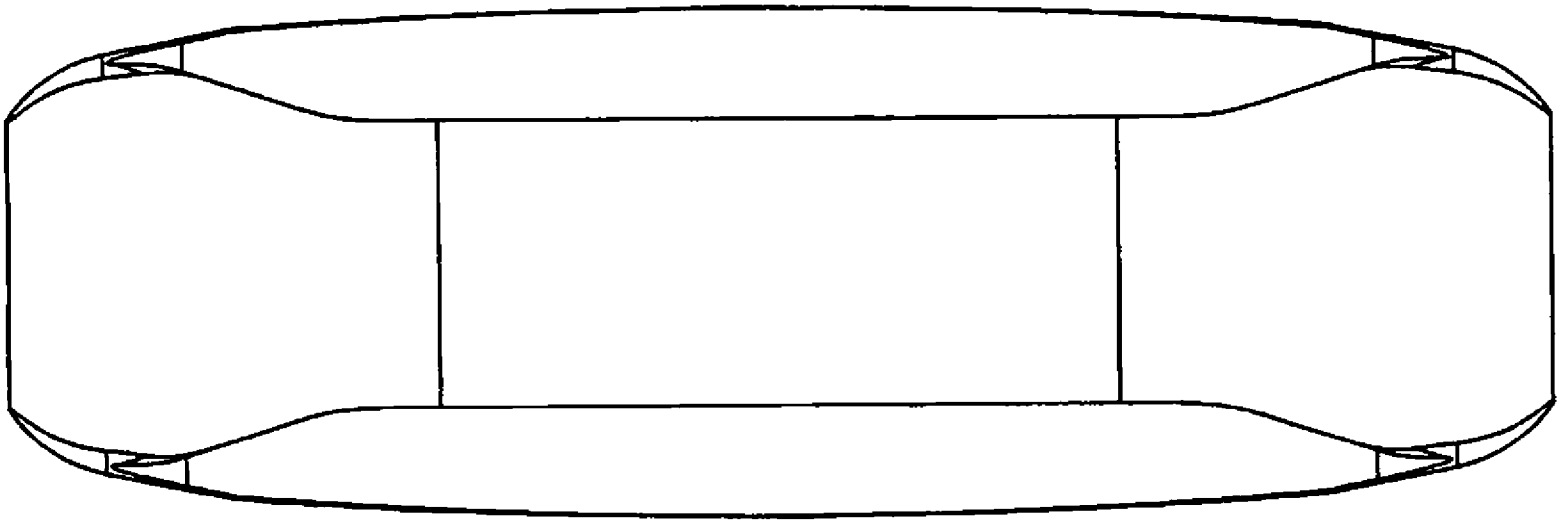
Figure 5C:
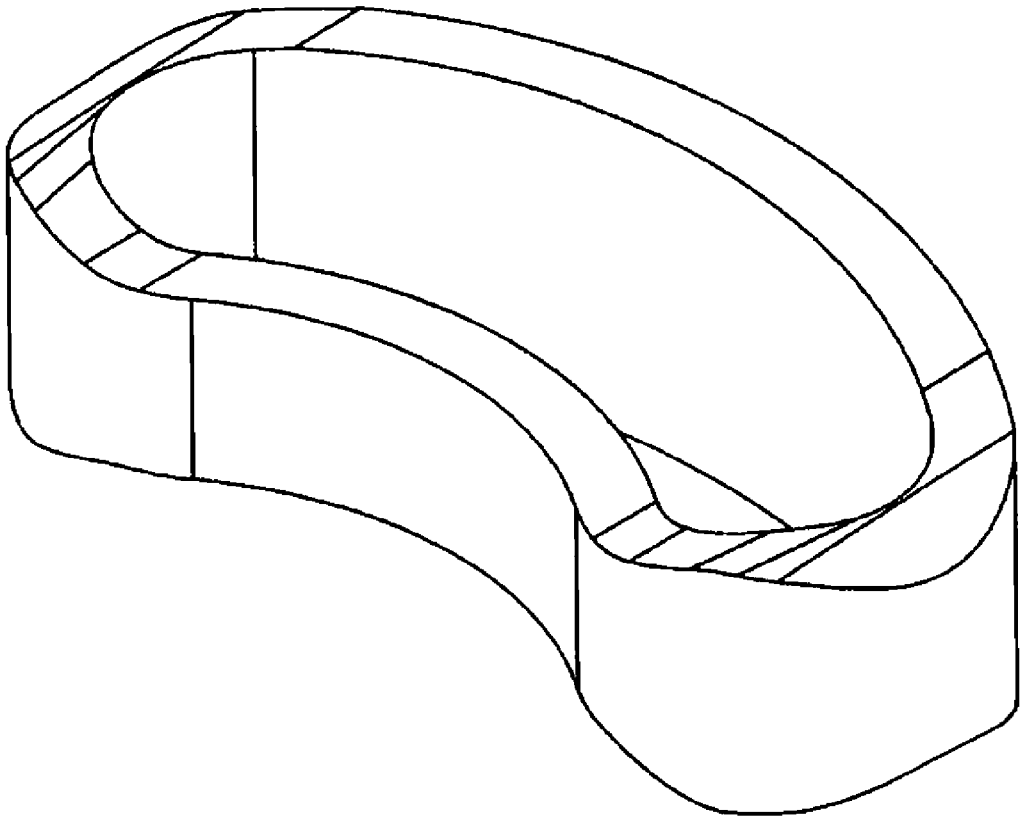

In embodiments particularly advantageous in the lumbar spine, the maximum height of the posterior wall is between about 5 mm and 18 mm., and the maximum thickness of the posterior wall is between about 1 mm and 3 mm. In some embodiments, such as FIGS. 1a-1g, the height of the posterior wall is such that it upper surface bears against the upper vertebral endplate. In other embodiments however, as in FIGS. 5a-5c, the height of the posterior wall is somewhat smaller and the upper and lower surfaces do not bear against the upper and lower endplates endplates.

Preferably, the horizontal cross section of the end wall is convexly curved. Such curves allow for smooth transition between the anterior and posterior walls and facilitate insertion into the disc space. Typically, the concave curve of the posterior wall is in the form of an arc having a radius of between 1.5 mm and 6.5 mm.

In some embodiments, at least one end wall is a leading end wall comprising a feature 121 adapted to engage an insertion instrument. This allows the cage to be inserted essentially lengthwise into a small opening in the posterior side of the disc space, and then rotated so that the anterior wall faces the anterior portion of the disc space.

In some embodiments, these features 121 comprise an opening adapted to receive a pusher instrument. In preferred embodiments, the opening is a threaded opening adapted to receive a threaded pusher instrument.

In some embodiments, the openings adapted to receive a pusher instrument are the sole openings in the end walls. This conditions conserves the mass of the end walls, and so provides greater strength to the structure.

In some embodiments, each end wall comprises a feature 121,123 adapted to engage an insertion instrument, thereby allowing each end wall to be a leading or trailing wall. This gives the surgeon extra flexibility. In some embodiments wherein each end wall comprises a feature 121,123 which is a hole adapted to engage an insertion instrument, the features are disposed asymmetrically about the centerline of the device (i.e., the features extend into the cage at different angles). In the case of FIG. 1a, the right hand hole 121 is disposed at an angle that is more orthogonal to planar wall 111 than the left hand hole 123. The asymmetric disposition of these features provide flexibility to the surgeon by accounting for differences in surgical technique, or size and location of their exposure, and anatomy.

Figure 2A:
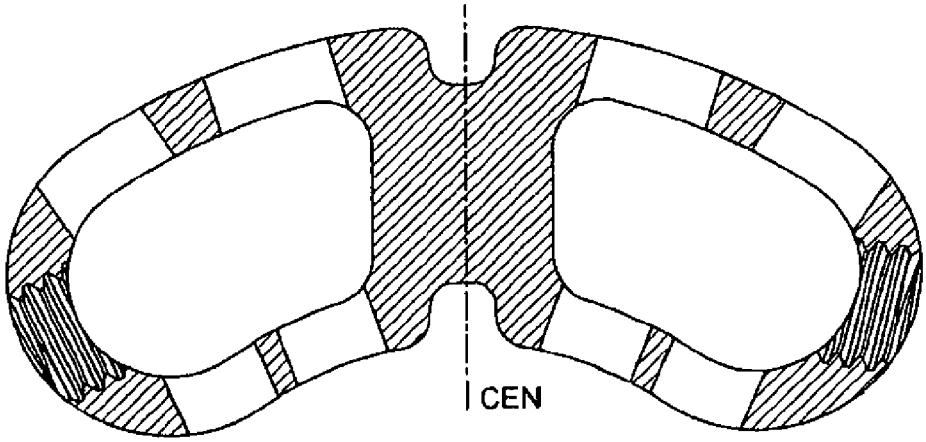
FIGS. 2a-2g disclose various views of a parallel banana shaped cage of the present invention.
Figure 2B:
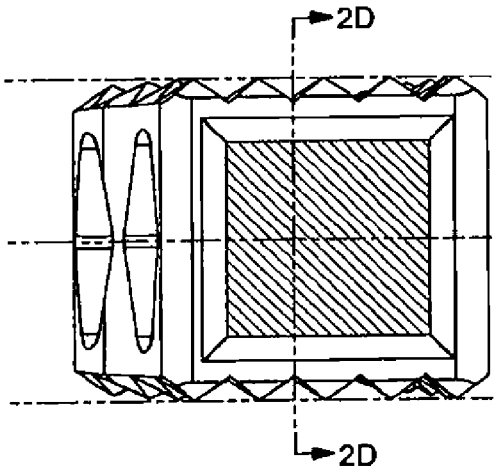
Figure 2C:
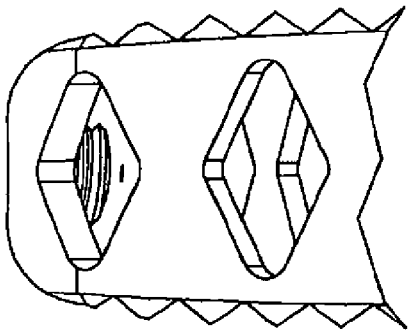
Figure 2D:
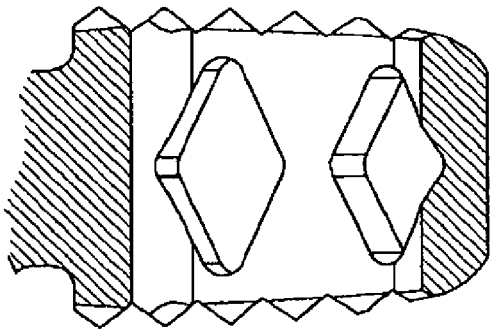
Figure 2E:
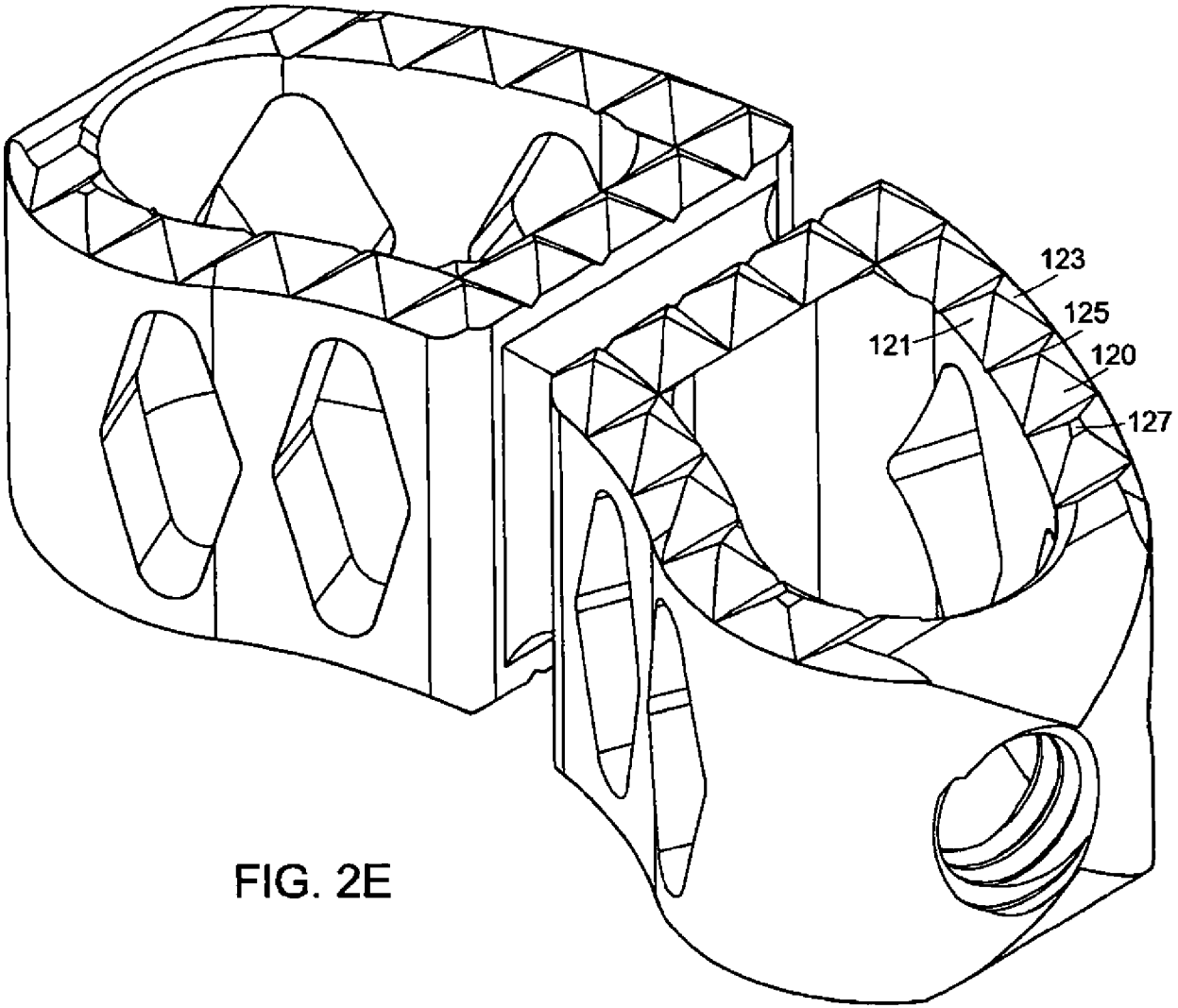
Figure 2F:
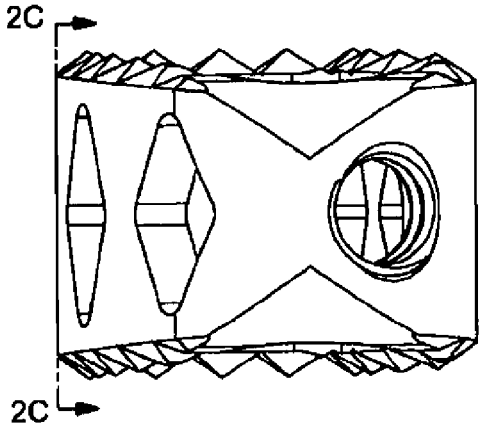
Figure 2G:
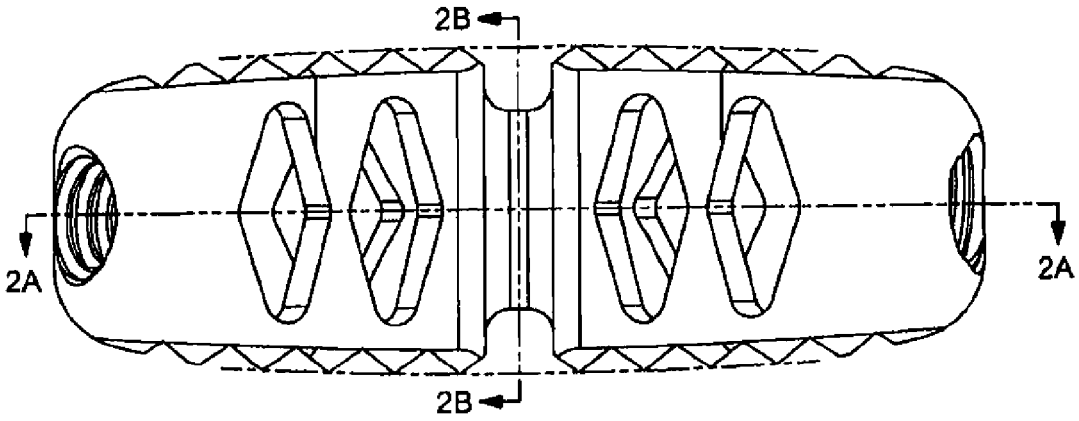

Therefore, in accordance with the present invention, there is provided an intervertebral fusion device comprising:

a) an anterior wall having a leading end and a trailing end b) a posterior wall having a leading end and a trailing end, c) a leading end wall connecting the leading ends of the anterior and posterior walls and having a leading insertion hole, d) a trailing end wall connecting the anterior and posterior walls and having a trailing insertion hole, wherein the anterior and posterior walls define a centerline therebetween (as shown by CEN in FIG. 2a), and wherein the leading and trailing insertion holes are disposed asymmetrically about the centerline.

Figure 9A:
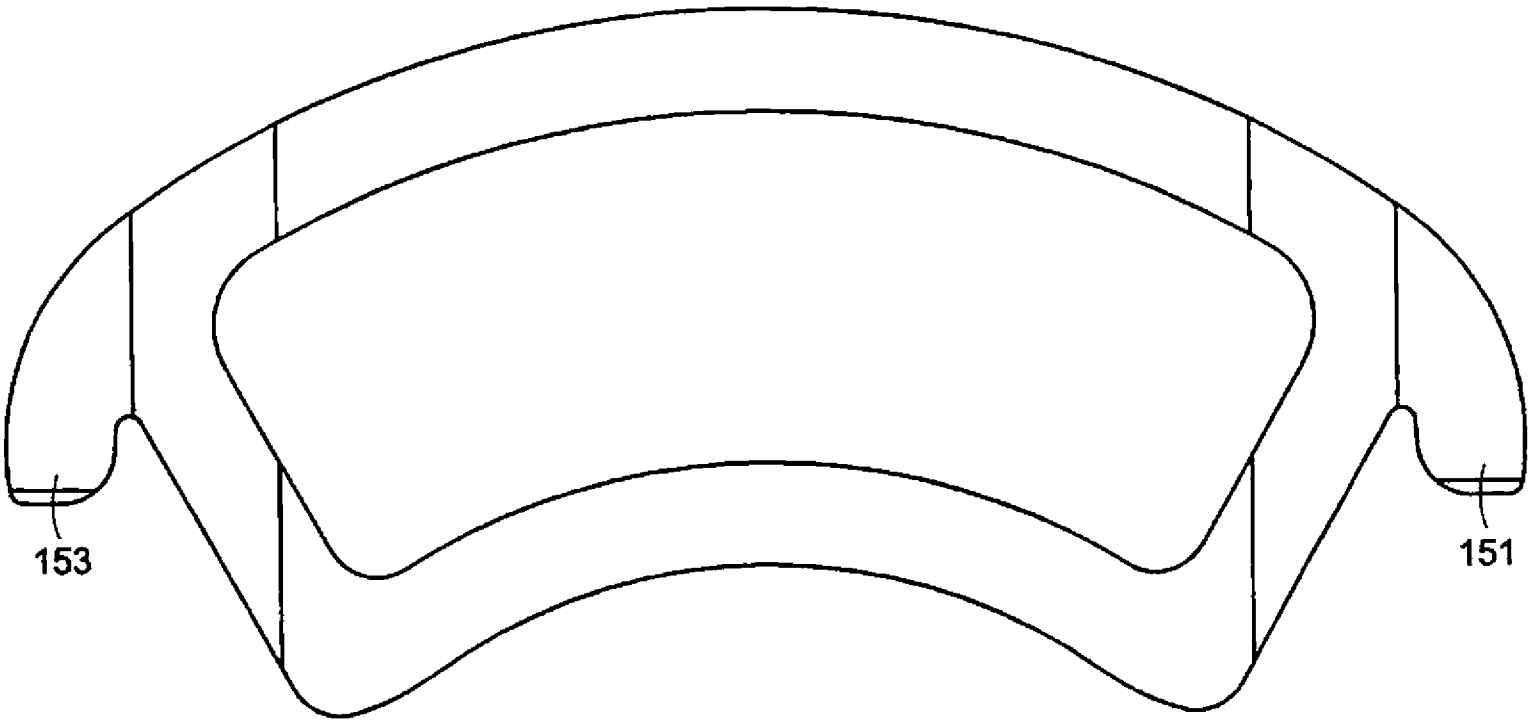
FIGS. 9a-9c disclose various views of a banana shaped cage of the present invention wherein the end walls comprises wings.
Figure 9B:
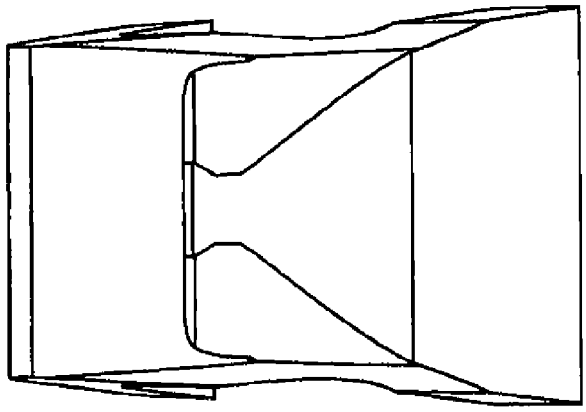
Figure 9C:
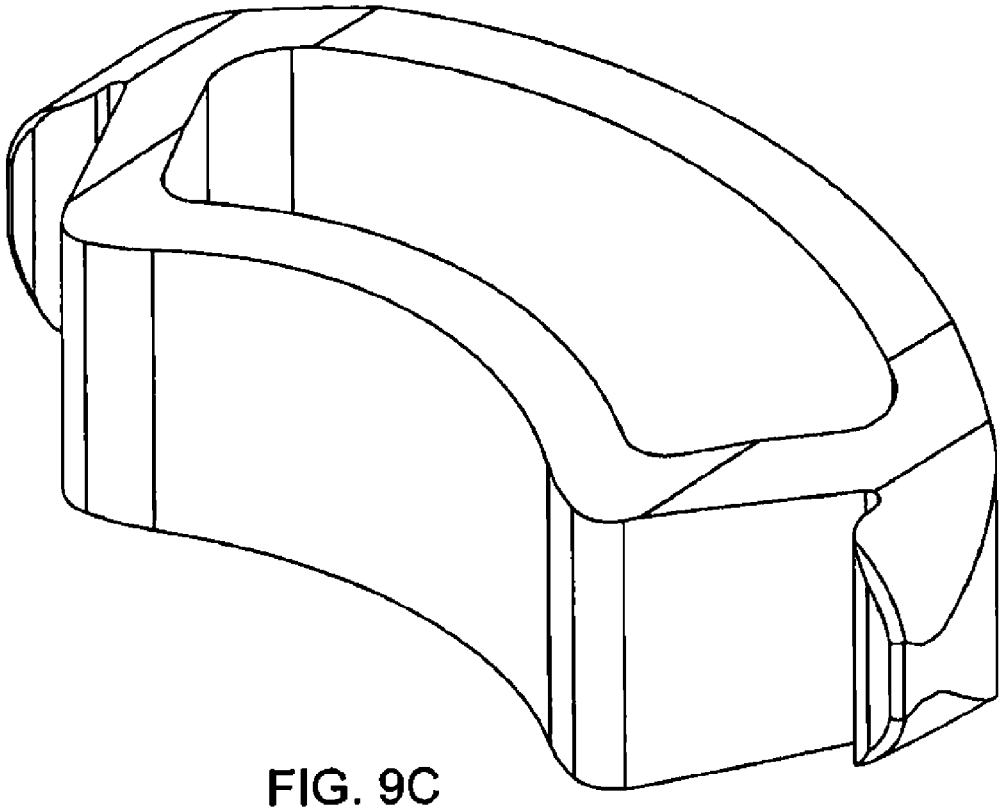

In some embodiments, as in FIGS. 9a-9c, the end walls form wings 151,153 extending tangentially from the normal curve of the anterior wall. This function of these wings is to extend the anterior wall and add increased support along the cortical rim.

Therefore, in accordance with the present invention, there is provided an intervertebral fusion device comprising:

a) an anterior wall having a convex shape, b) a posterior wall, c) first and second end walls between (and preferably connecting) the anterior and posterior walls, d) an upper bearing surface between the anterior and posterior walls (and preferably having an anterior portion above the anterior wall, and a posterior portion above the posterior wall), and at least one upper opening therethrough adapted to promote bony fusion, and e) a lower bearing surface having an anterior portion below the anterior wall, a posterior portion below the posterior wall, and at least one lower opening therethrough adapted to promote bony fusion, wherein the end walls form wings extending tangentially from the normal curve of the anterior wall.

Preferably, the vertical cross section of the leading end wall is tapered to facilitate entry of the device into the disc space. Preferably, each end wall is tapered, so that the surgeon can used either end wall as the leading end wall. More preferably, the taper provides a bullet shape. The bulleted end distracts the vertebral bodies upon insertion and deflects any impending soft tissue.

The upper and lower surfaces of the cage are adapted to bear against the opposing surfaces of the opposing vertebral bodies defining the disc space. In some embodiments, the upper and lower surfaces are adapted to bear against the endplate portion of the vertebral bodies. In others, channels are cut in the endplates, and these surfaces are adapted to bear against the opposed bone surfaces exposed by these channels.

Preferably, each of the upper and lower surfaces are convexly curved in a lateral-lateral cross section. More preferably, each is shaped to conform to the shape of the opposed surfaces of the vertebral endplates. When the upper and lower surfaces are so shaped, the cage conforms more precisely to the disc space. Typically, the convex curve of the upper and lower surfaces is in the form of an arc having a radius of between 90 mm and 240 mm.

In some embodiments, the upper and lower surfaces comprise openings 175, 195 adapted to promote bone fusion therethrough.

In some embodiments, these openings have a length and a width, wherein the length of the opening is greater than the width of the opening. Since the preferred cages have a long length, in this condition, only a few openings need be filled from the top or bottom in order to desirably fill the cage with graft material.

In some embodiments, the openings comprises between about 30 areal % and about 60 areal % of the upper and lower bearing surfaces. In contrast to the Frey structure, whose upper and lower openings comprises roughly about 70 to 80 areal percent of the upper and lower surfaces, these embodiments of the present invention have more mass and so provide greater strength to the structure and increased resistance to subsidence than the Frey structure. This enhanced strength is important because the overall size of the device of the present invention is typically smaller than that of the Frey device.

In some embodiments, as in FIGS. 1a-1g, the horizontal cross section of each of the upper and lower surfaces comprises a recessed portion 76,96, thereby defining right 77,97 and left 79,99 upper and lower surface portions. The function of the recessed portion is to from an I-beam structure to help prevent bending during insertion. It can also be used for alignment, for post-operative visualization of the extent of fusion at the endplate-cage interface, and may help resist subsidence.

In embodiments particularly advantageous in the lumbar spine, the maximum length of each of the upper and lower surfaces is between about 20 mm and 30 mm.

Figure 7A:
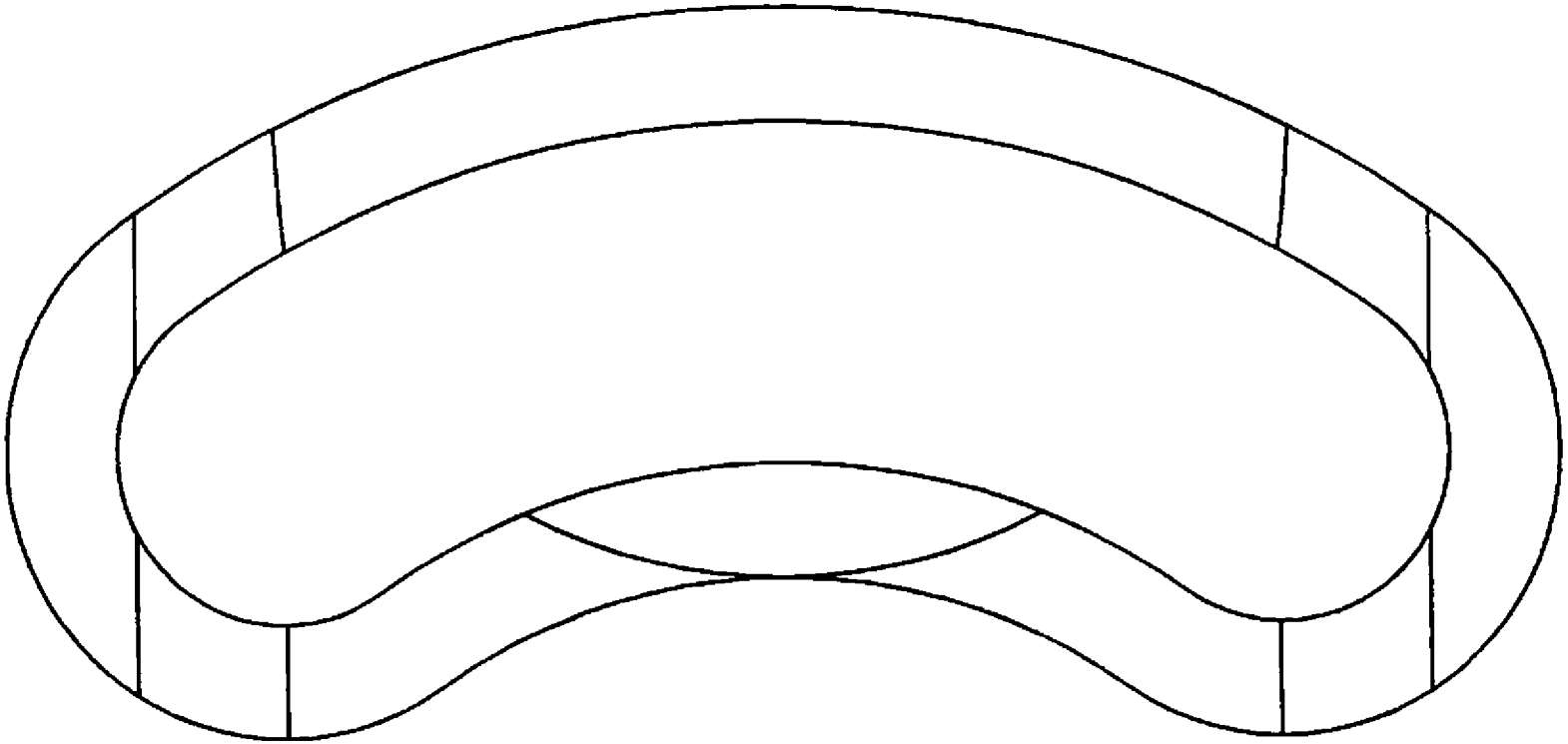
FIGS. 7a-7c disclose various views of a parallel banana shaped cage of the present invention only a portion posterior wall has a height equalling the corresponding height of the anterior wall.
Figure 7B:
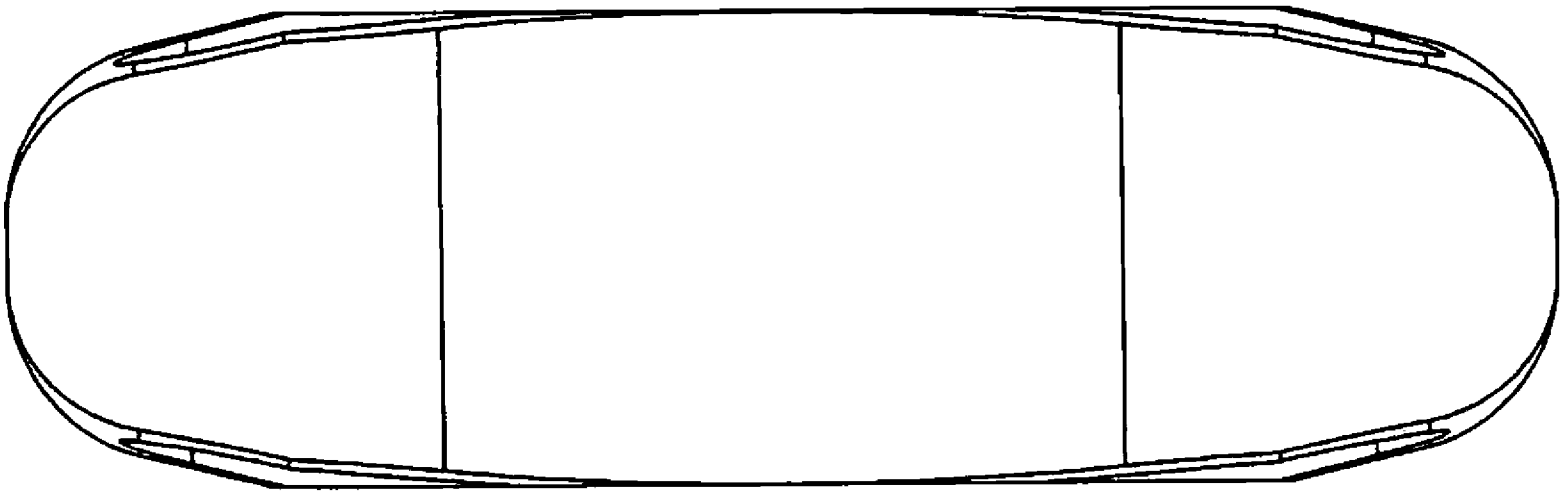
Figure 7C:
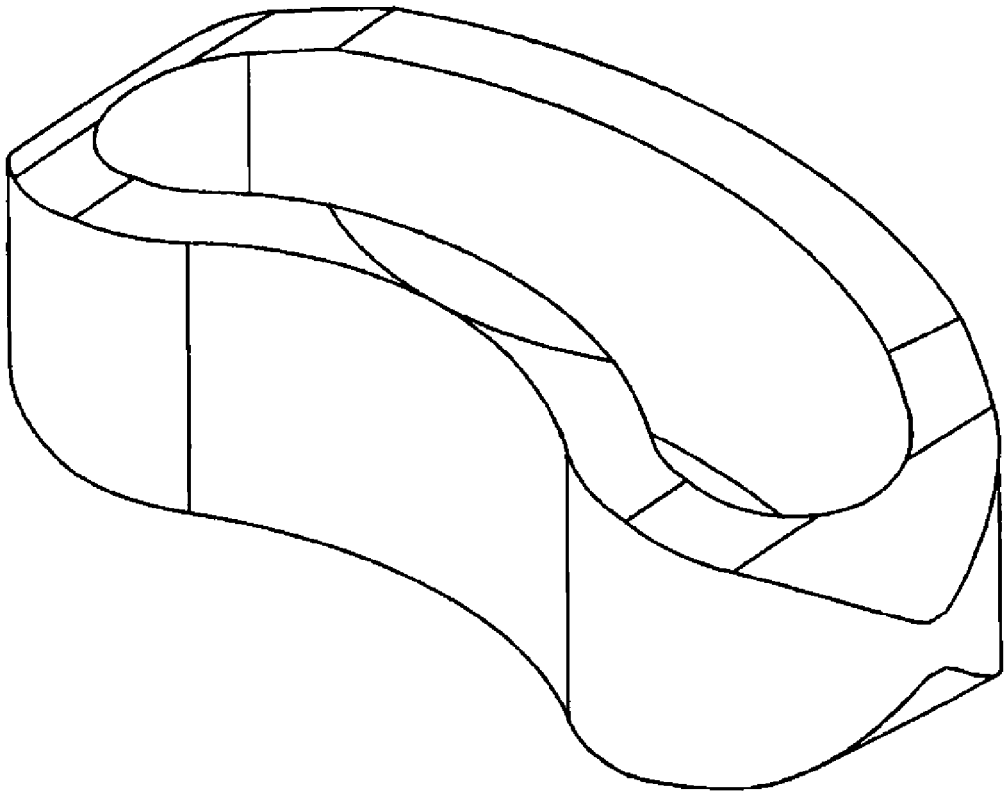

In some embodiments, as in FIGS. 2a-2g, the maximum height of the anterior wall equals the corresponding maximum height of the posterior wall, such that the upper and lower bearing surfaces are parallel. In the particular design of FIGS. 7a-7c, less than one half of the posterior wall is parallel with the anterior wall, with the remainder having a somewhat smaller corresponding height.

Figure 6A:
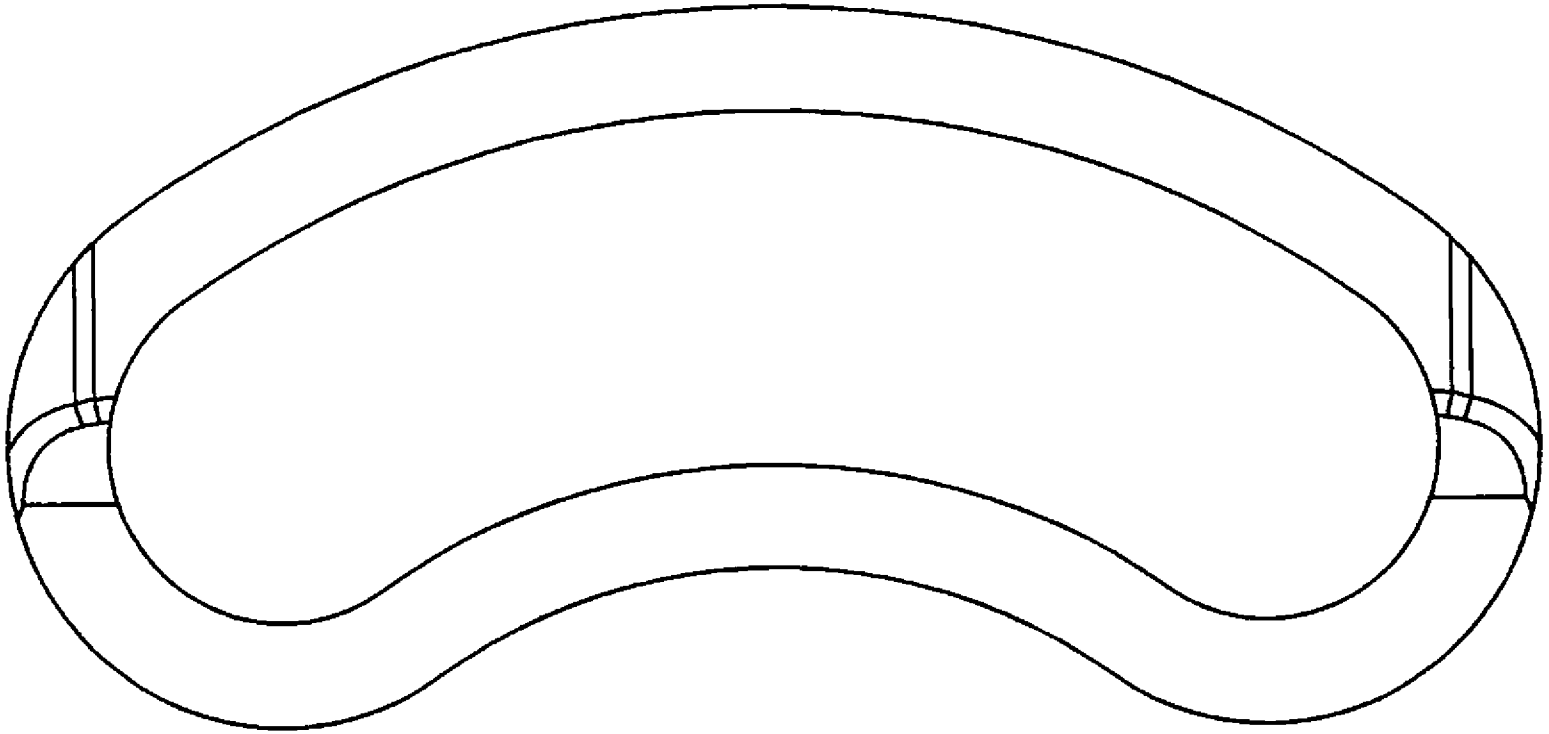
FIGS. 6a-6c disclose various views of another lordotic banana shaped cage of the present invention.
Figure 6B:
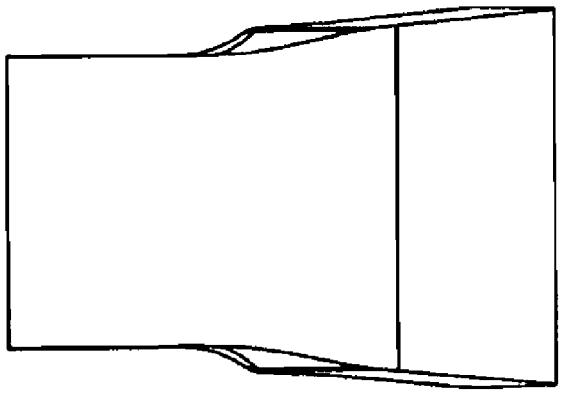
Figure 6C:
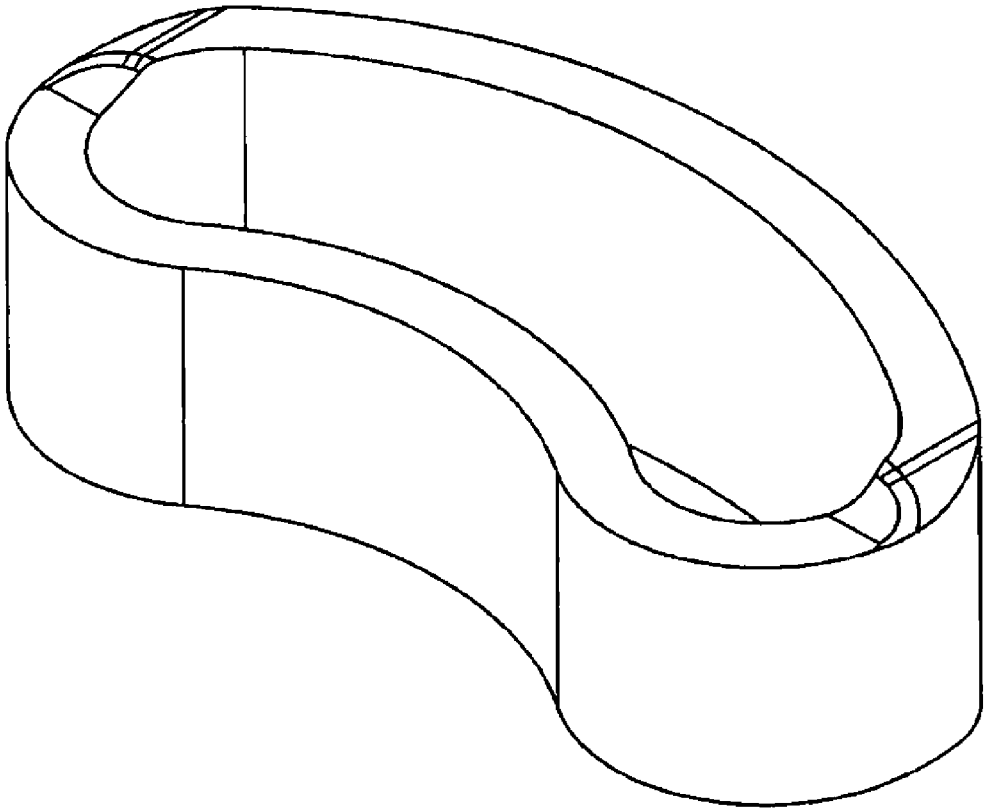

In some embodiments, as in FIGS. 1a-1g, the maximum height 401 of the anterior wall is greater than the maximum height 403 of the posterior wall, such that the upper and lower bearing surfaces provide lordosis. Preferably, the heights are such that the lordosis created is between about 1 degree and about 10 degrees. This range corresponds to the natural physiologic range of lordosis in the lumbar and cervical portions of the spine. In some embodiments, upper and lower surfaces are linearly graded so that the lordotic angle is consistent from the anterior wall to the posterior wall. In other embodiments, the grade can be provided essentially entirely in the anterior wall, or as in FIGS. 6a-6c, the grade can be provided essentially entirely in the anterior and end walls.

In some embodiments, the maximum height of the anterior wall is less than the maximum height of the posterior wall, such that the upper and lower bearing surfaces provide kyphosis. Preferably, the heights are such that the kyphosis created is between about 1 degree and about 10 degrees. This range corresponds to the natural physiologic range of kyphosis in the thoracic portion of the spine.

Therefore, in accordance with the present invention, there is provided intervertebral fusion device comprising:

a) an anterior wall having a convex shape and a maximum height, b) a posterior wall having a concave shape and a maximum height, c) first and second end walls connecting the anterior and posterior walls, wherein the maximum height of the anterior wall is less than the maximum height of the posterior wall.

In some embodiments, the anterior wall has a middle portion 301 having a maximum height 401 and lateral end portions 305 each having a maximum height 405, and the maximum height of the middle portion is greater than the maximum height of the lateral end portions. This provides an advantageous doming effect that corresponds to the height of a natural disc space.

In some embodiments, the upper and lower bearing surfaces formed teeth 120 adapted to grip the vertebral endplates and resist cage dislocation. These teeth comprise two angled bearing surface portions 121, 123 that form an angle adapted for gripping the endplates. In some embodiments, the angled bearing surface portions 121, 123 meet to form a sharp point 125. In other embodiments, a land 127 is disposed between the angled bearing surface portions 121, 123. The angled nature of the teeth provides a gripping surface that is superior to the grooves formed from essentially parallel surfaces provided in the Frey cage.

Therefore, in accordance with the present invention, there is provided an intervertebral fusion device comprising:

a) an anterior wall having a convex horizontal cross section, b) a posterior wall, c) first and second end walls between (and preferably connecting) the anterior and posterior walls d) an upper bearing surface between the anterior and posterior walls (preferably, having an anterior portion above the anterior wall and a posterior portion above the posterior wall), and e) a lower bearing surface between the anterior and posterior walls (preferably, having an anterior portion below the anterior wall and a posterior portion below the posterior wall), and f) first and second transverse struts extending from the anterior portion of the upper bearing surface to the posterior portion of the upper bearing surface, wherein the upper and lower bearing surfaces form teeth extending from each of the transverse struts and adapted to grip the vertebral endplates.

Figure 8A:
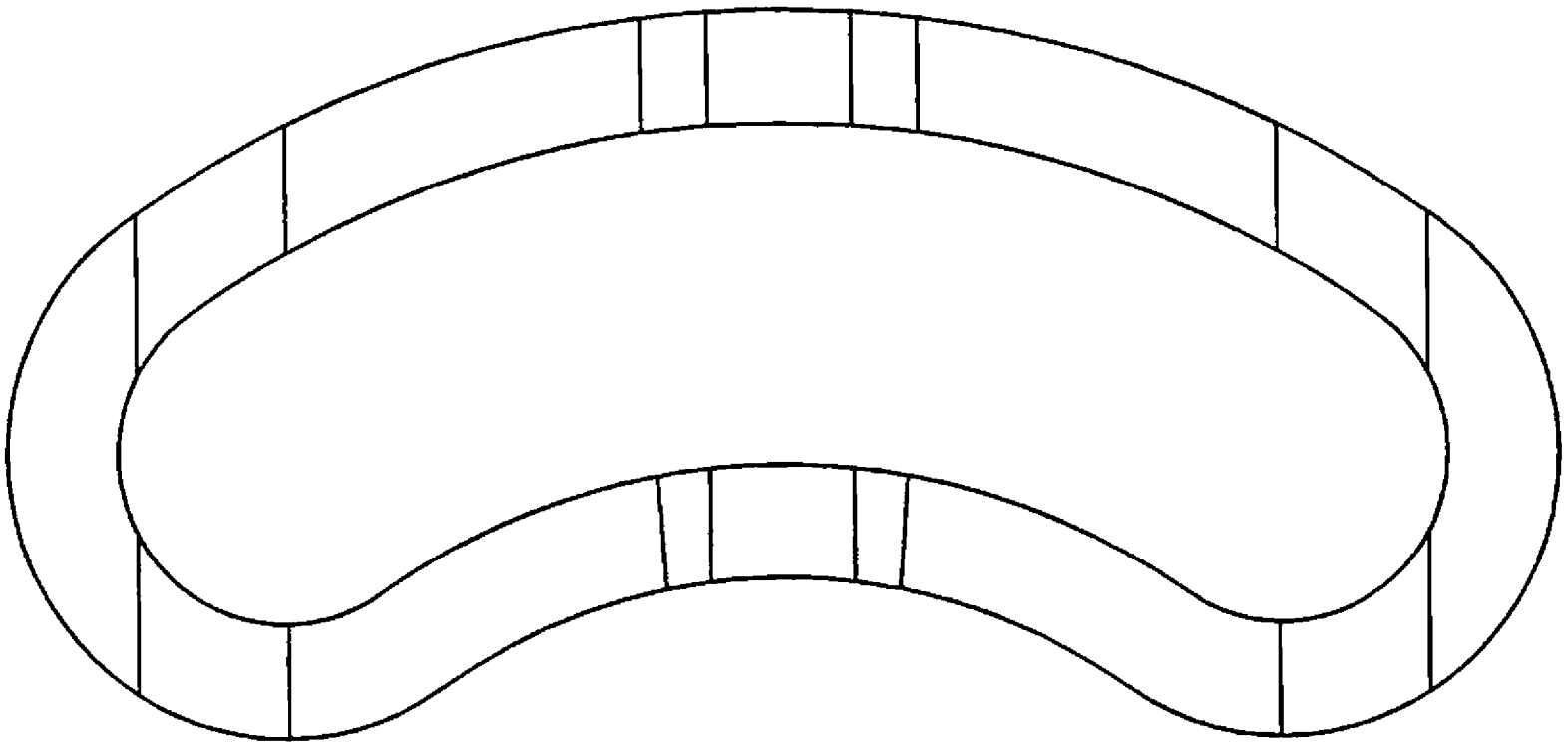
FIGS. 8a-8c disclose various views of a banana shaped cage of the present invention wherein the anterior wall comprises upper and lower ridges.
Figure 8B:
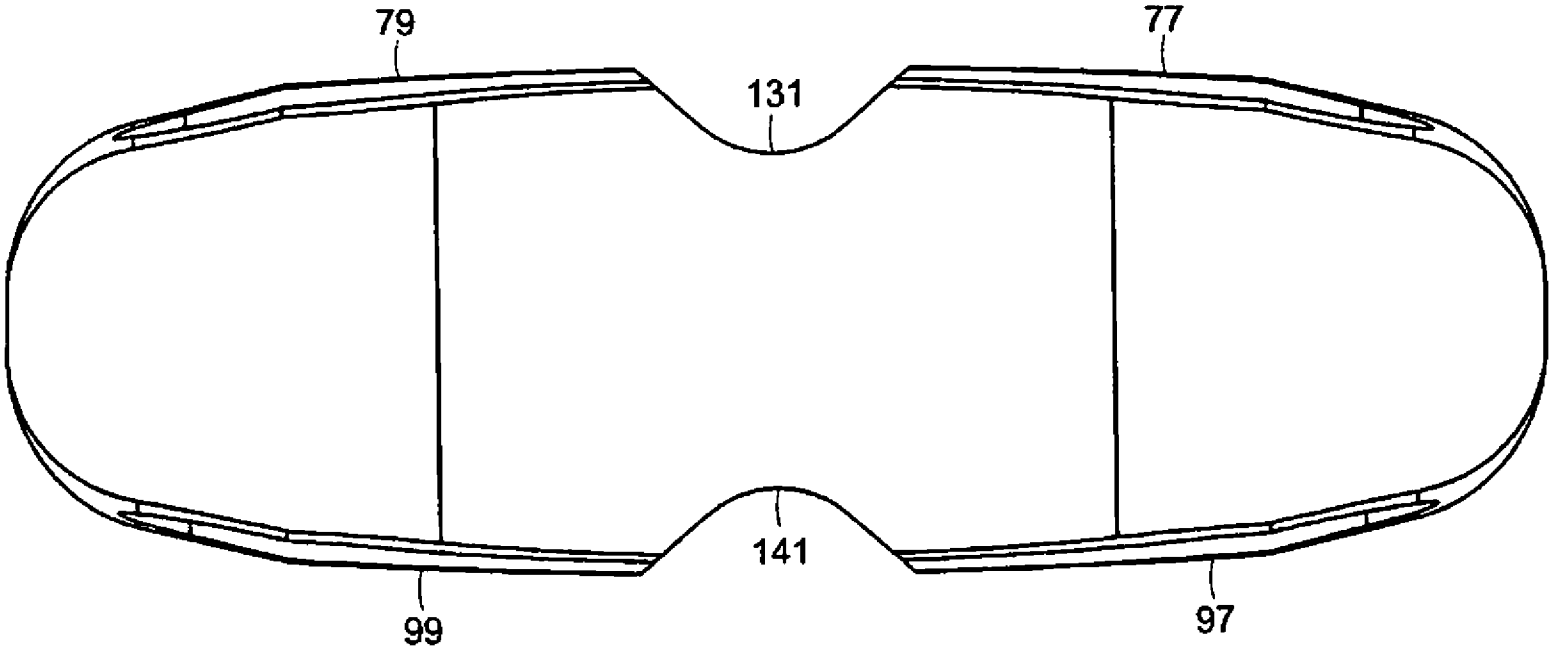
Figure 8C:
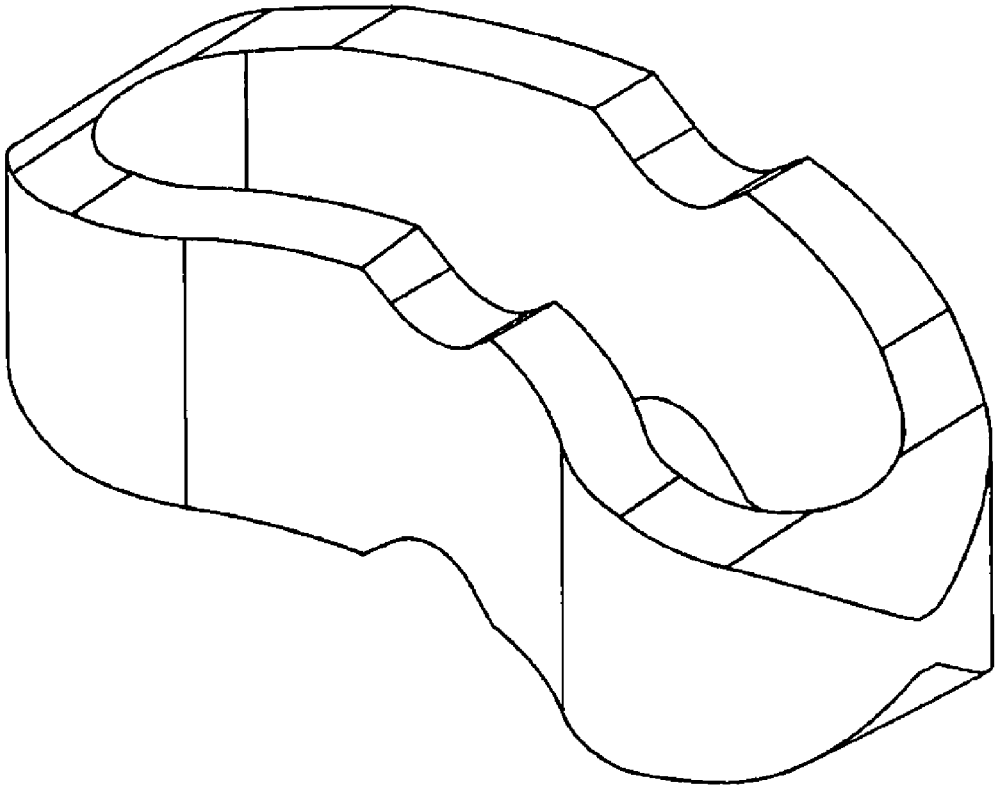

In some embodiments, as in FIGS. 8a-8c, the vertical cross section of each of the upper and lower surfaces comprises a recessed ridge portion 131, 141, thereby defining right 77, 97 and left 79,99 upper and lower surface portions. The function of this ridge is to define a left and a right side of the implant to increase the stability of the implant (like the channel of FIGS. 1a-1h), as well as provide a notch to access the progression of the fusion.

Therefore, in accordance with the present invention, there is provided an intervertebral fusion device comprising:

a) an anterior wall having a convex shape, and a maximum height, b) a posterior wall having a concave shape, a middle portion of substantially uniform height, lateral end portions, c) first and second end walls connecting the anterior and posterior walls d) an upper bearing surface between the anterior and posterior walls (preferably, having an anterior portion above the anterior wall, and a posterior portion above the posterior wall), having a middle portion having a recessed ridge, lateral end portions, and at least one upper opening therethrough adapted to promote bony fusion, and e) a lower bearing surface having an anterior portion below the anterior wall, a posterior portion below the posterior wall, and at least one lower opening therethrough adapted to promote bony fusion.

In some embodiments, the openings in the exterior surfaces of the cage extend into the cage to create a chamber 151, 153 therein. This chamber is adapted to hold bone graft material therein and promoting bone fusion therethrough. In some embodiments, the center strut defines dual chambers whose reduced size provides for easier retention of the graft than a single larger chamber.

In preferred embodiments, the cage comprises at least one strut 101 extending from the anterior portion of the upper bearing surface to the posterior portion of the upper bearing surface. This strut helps stabilize the cage and increases the mechanical strength of the cage.

In some embodiments, the cage comprises first 101 and second 103 transverse struts extending from the anterior portion of the upper bearing surface to the posterior portion of the upper bearing surface. The use of two struts helps prevent medial-lateral rocking of the cage about its midline (as would be the case with a single strut).

Therefore, in accordance with the present invention, there is provided an intervertebral fusion device adapted for non-linear insertion comprising:

a) an anterior wall having a convex shape, b) a posterior wall, c) first and second end walls connecting the anterior and posterior walls d) an upper bearing surface having an anterior portion above the anterior wall and a posterior portion above the posterior wall, and e) a lower bearing surface having an anterior portion below the anterior wall and a posterior portion below the posterior wall, and f) first and second transverse struts extending from the anterior portion of the upper bearing surface to the posterior portion of the upper bearing surface.

In some embodiments, the first 101 and second 103 struts are part of a larger internal planar wall 111 extending transverely from the anterior wall to the posterior wall. This internal planar wall effectively splits the cage into right and left portions having right and left graft chambers. This is advantageous when the internal wall is disposed near the centerline of the cage because the smaller chambers can more effectively hold graft material compressed therein than a single large chamber.

Figure 4A:
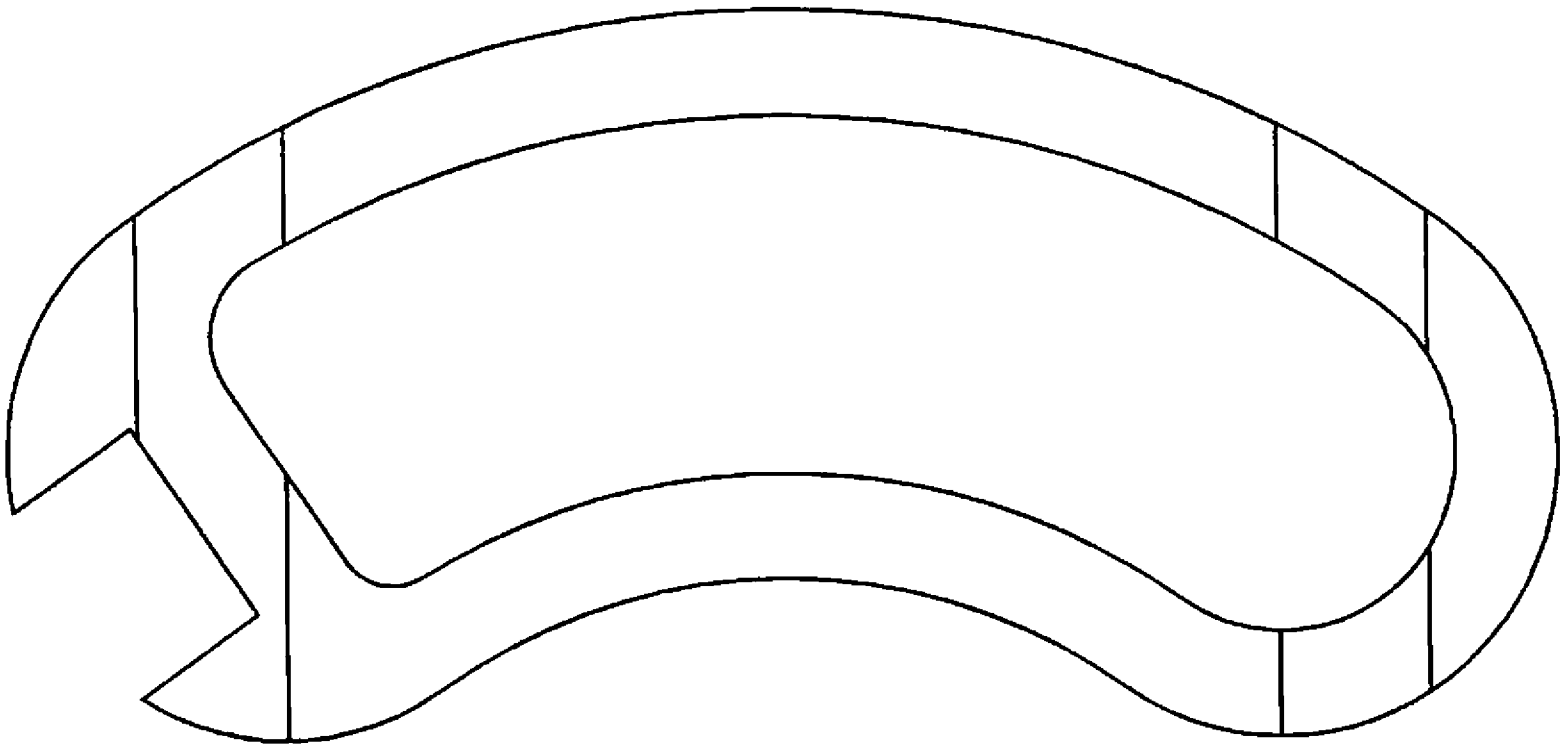
FIGS. 4a-4c disclose various views of a banana shaped cage of the present invention having an internal planar wall disposed near an end wall.
Figure 4B:
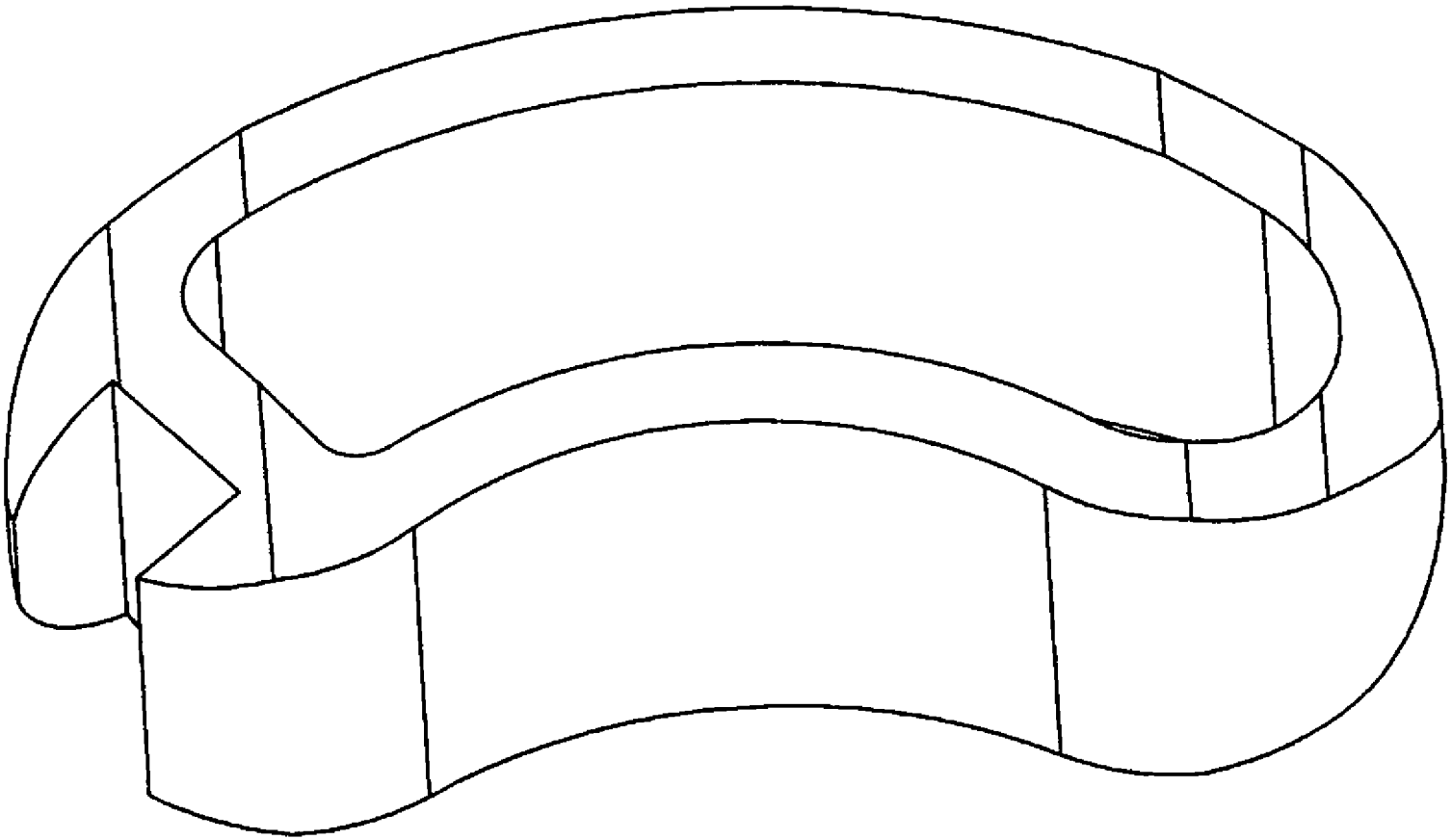
Figure 4C:
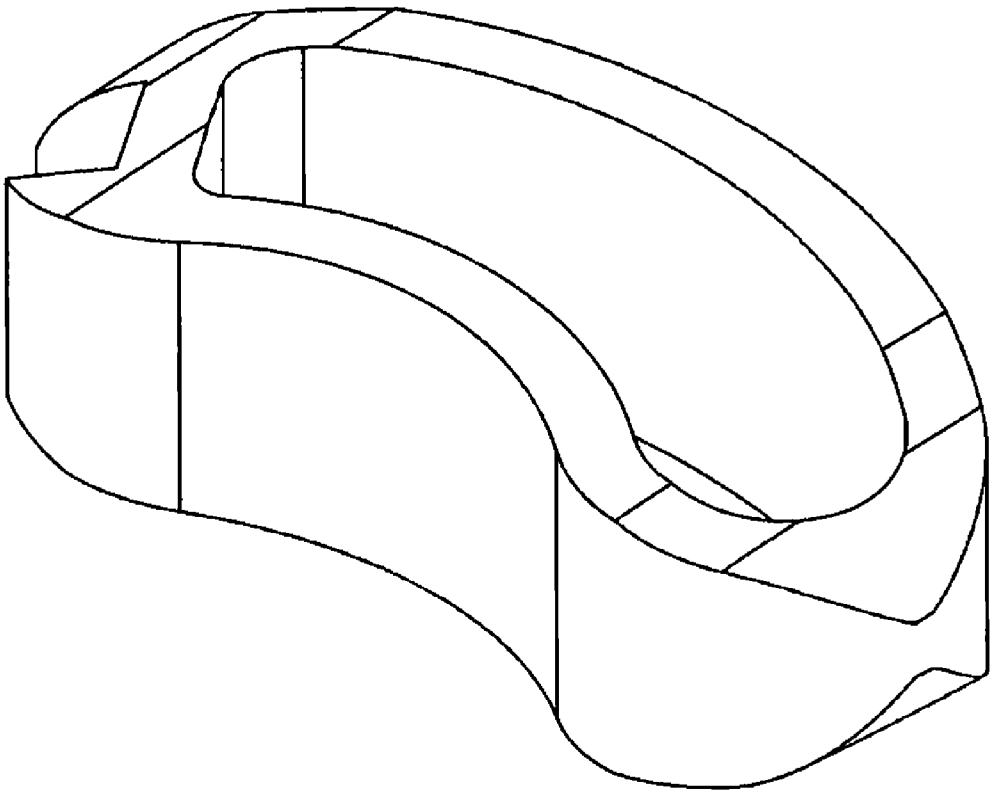

In some embodiments, as in FIGS. 4a-4c, the internal planar wall is disposed near an end wall of the cage.

Figure 10A:
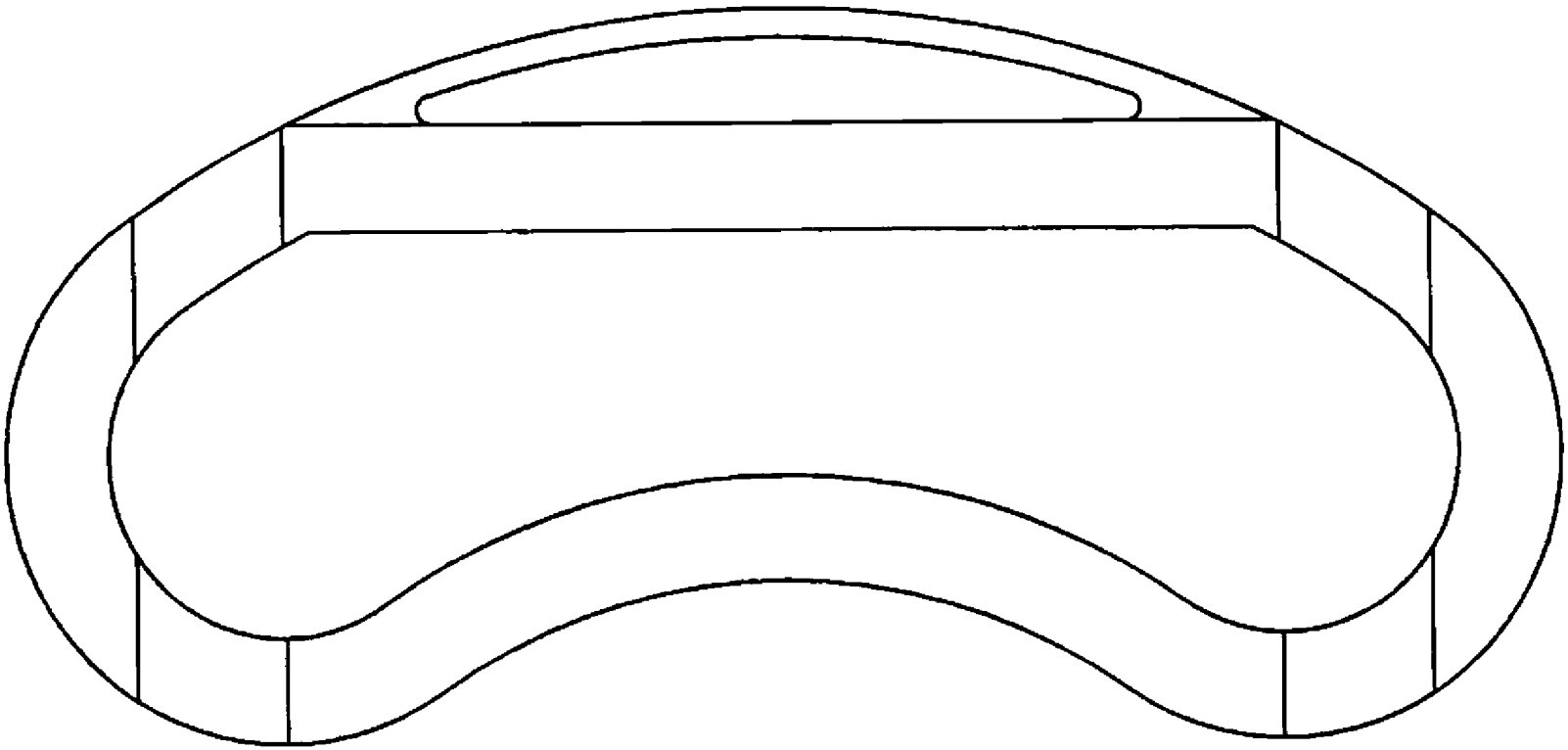
FIGS. 10a-10c disclose various views of a banana shaped cage of the present invention having a belt disposed anterior to the anterior wall.
Figure 10B:
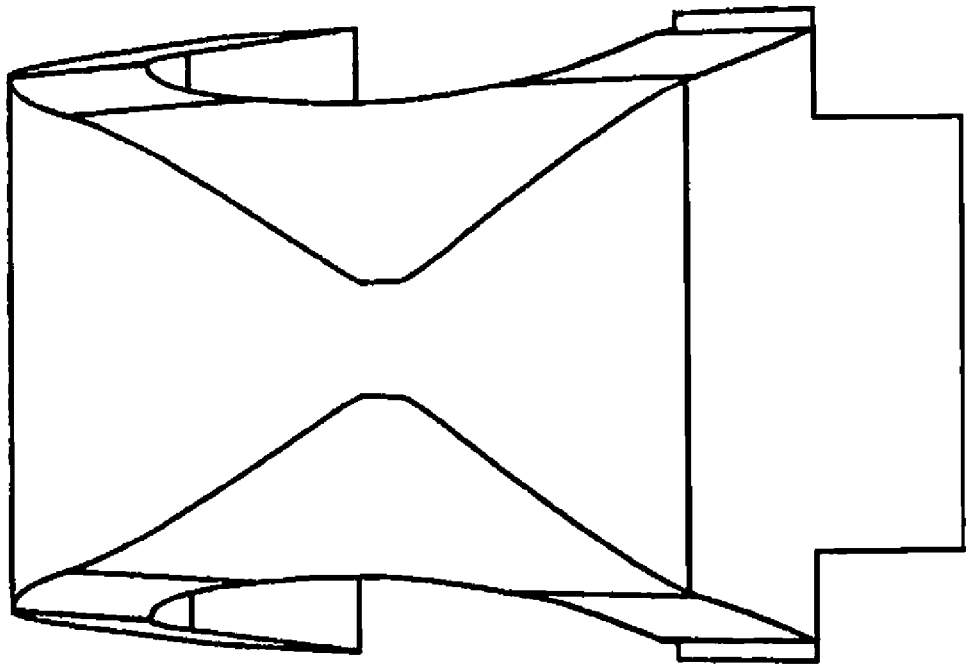
Figure 10C:
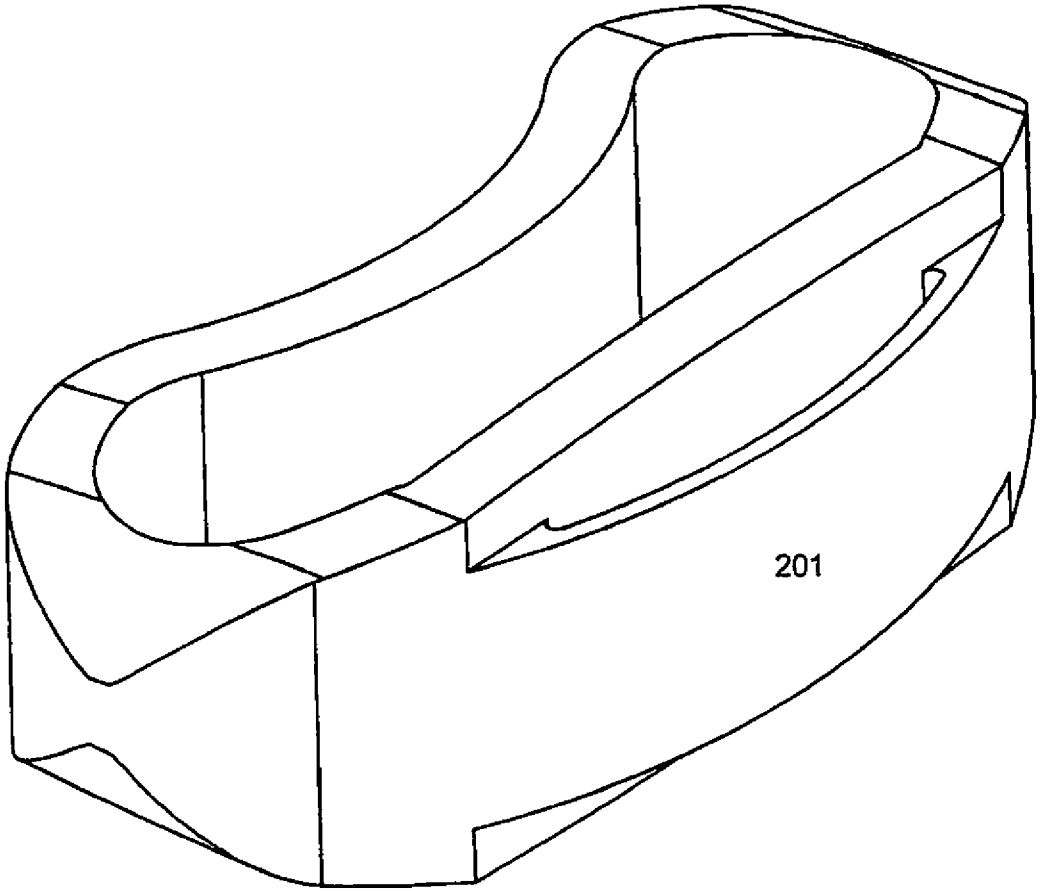

In some embodiments, as in FIGS. 10a-10c, the device further comprises a horizontally disposed belt 201 extending anteriorly from anterior wall. The function of this belt is to mate with an insertion instrument to facilitate insertion, or to mate with a guide instrument to facilitate alignment.

Therefore, in accordance with the present invention, there is provided an intervertebral fusion device comprising:

a) an anterior wall having a convex shape, b) a posterior wall, c) first and second end walls connecting the anterior and posterior walls d) an upper bearing surface between the anterior and posterior walls (preferably, having an anterior portion above the anterior wall, and a posterior portion above the posterior wall), and at least one upper opening therethrough adapted to promote bony fusion, and e) a lower bearing surface between the anterior and posterior walls (preferably, having an anterior portion below the anterior wall, a posterior portion below the posterior wall), and, preferably, at least one lower opening therethrough adapted to promote bony fusion, and f) a horizontally disposed ridge (preferably, a belt) extending anteriorly from anterior wall.

The device of the present invention may be manufactured from any biocompatible material commonly used in interbody fusion procedures.

In some embodiments, the cage is made from a composite comprising:

a) 40-99% polyarylethyl ketone PAEK, and b) 1-60% carbon fiber wherein the polyarylethyl ketone PAEK is selected from the group consisting of polyetherether ketone PEEK, polyether ketone ketone PEKK, polyether ketone ether ketone ketone PEKEKK, and polyether ketone PEK.

Preferably, the carbon fiber is chopped. Preferably, the PAEK and carbon fiber are homogeneously mixed. Preferably, the composite consists essentially of PAEK and carbon fiber. Preferably, the composite comprises 60-80 wt % PAEK and 20-40 wt % carbon fiber, more preferably 65-75 wt % PAEK and 25-35 wt % carbon fiber. In some embodiments, the cage is made from materials used in carbon fibers cages marketed by DePuy AcroMed, Raynham, Mass., USA. In some embodiments, the composite is PEEK-OPTIMA™, available from Invibio of Greenville, N.C.

In other embodiments, the cage is made from a metal such as titanium alloy, such as Ti-6A1-4.

In other embodiments, the cage is made from an allograft material.

In some embodiments, the cage is made from ceramic, preferably a ceramic that can at least partially be resorbed, such as HA or TCP. In other embodiments, the ceramic comprises an oxide such as either alumina or zirconia.

In some embodiments, the cage is made from a polymer, preferably a polymer that can at least partially be resorbed, such as PLA or PLG.

In some embodiments, the cage is provided in a sterile form.

In some embodiments, autologous bone graft material obtained from the iliac crest of the human patient is inserted into the chamber of the cage.

In other embodiments, bone graft material made from allograft particles such as cancellous chips and demineralized bone matrix may be used.

In other embodiments, concentrated osteoinductive materials such as autologous platelet rich plasma or recombinant growth factors may be used.

In other embodiments, concentrated osteogenetic materials such as autologous mesenchymal stem cells (MSCs) or recombinant MSCs may be used.

Preferably, the device of the present invention is placed within the disc space so that the entire device rests within the anterior third of the disc space (ie., the anterior aspect of the disc space). More preferably, the device of the present invention is placed within the disc space so that the entire device rests within the anterior fifth of the disc space, more preferably the anterior eighth of the disc space.

Therefore, in accordance with the present invention, there is provided an intervertebral fusion device comprising:

a) an anterior wall and a posterior wall defining a width therebetween, b) first and second end walls connecting the anterior and posterior walls and defining a length therebetween, wherein the anterior wall has a middle portion, lateral end portions, each having a maximum height, and the maximum height of the middle portion is greater than the maximum height of the lateral end portions, wherein the width of the device is less than the length of the device, and wherein the length is less than ½ the width of the disc space The device of the present invention is intended for non-linear insertion into the intervertebral space through a variety of techniques and approaches, commonly using a single unilateral approach to the disc space.

The design of the implant aids in its safe and efficient insertion into the intervertebral space, and allows for a symmetric single-cage solution to the interbody procedure.

Figure 11A:
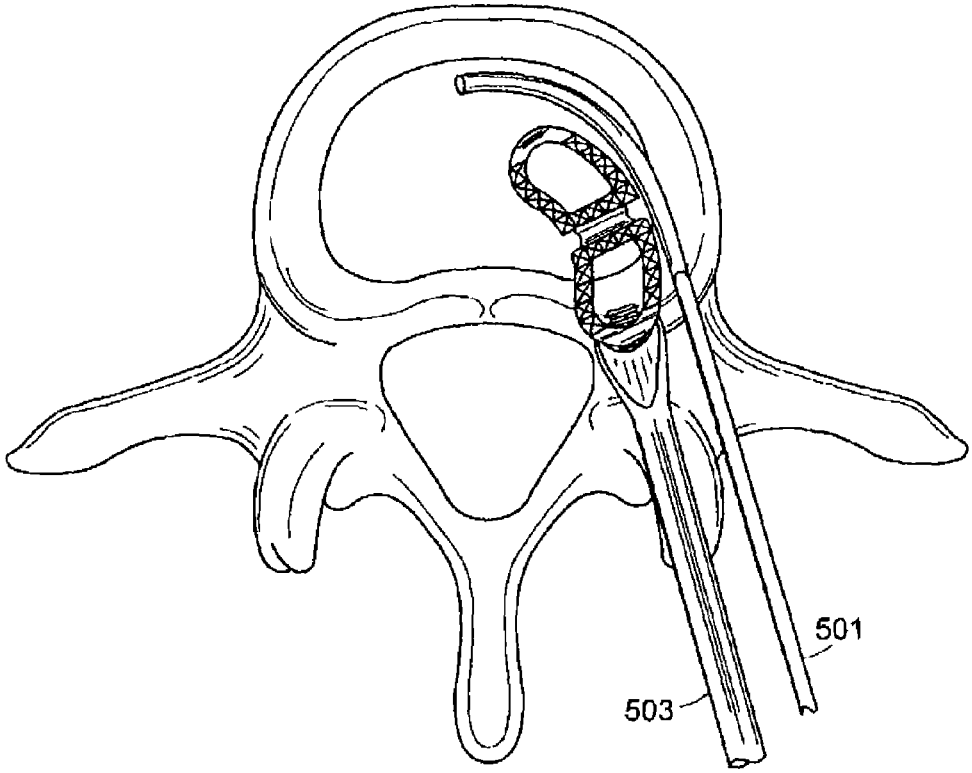
FIGS. 11a-11d disclose the insertion of a banana shaped cage of the present invention into a disc space.

Now referring to FIG. 11a, once the intervertebral disc material has been completely removed and the vertebral endplates prepared with a curved rasp (not shown), a rail 501 is inserted into the disc space to act as a guide for selected trials and the implant. The disclosed rail is a curved guide or ramp designed to steer the cage into proper positioning. The curvature of the rail roughly matches the curvature of the anterior wall of the implant.

Next, a trial (not shown) may be used to determine the appropriate implant size and degree of lordosis.

Next, an Inserter 503 is then attached to one of the implant's two insertion holes according to surgical approach and patient anatomy. These threaded insertion holes are asymmetric about the center of axis of the implant to provide for two different angles of insertion. The trials provide this same option.

The implant is then placed into a cage filler block (not shown) and packed with either autologous bone graft or a substitute.

Figure 11B:
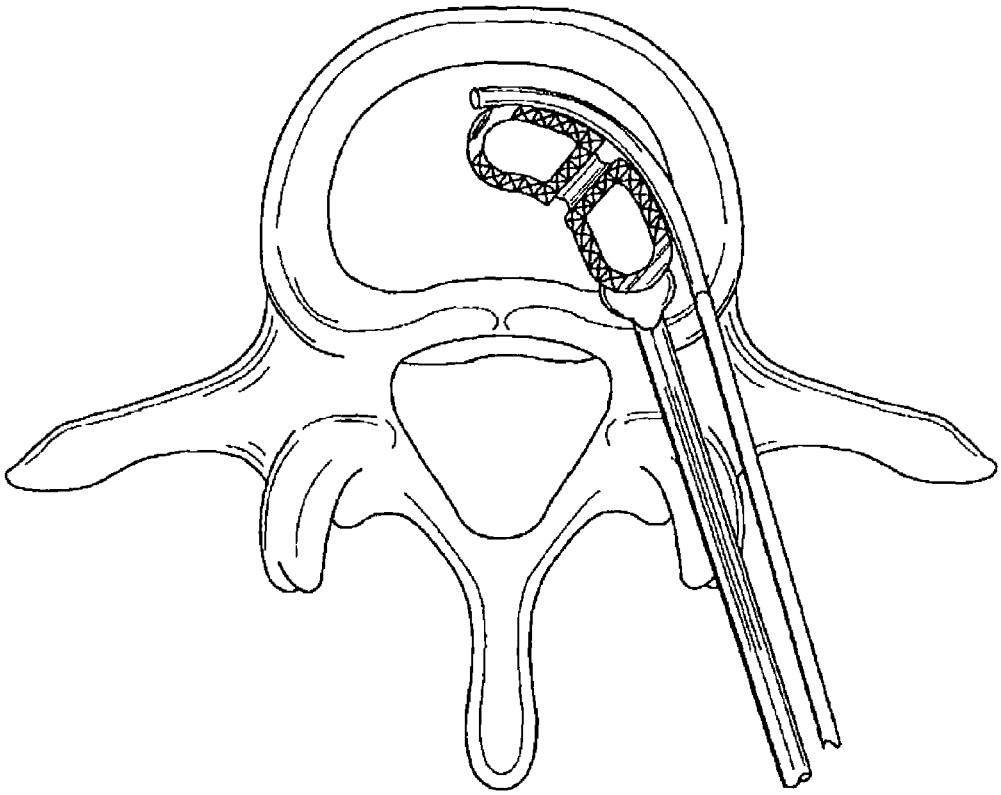
Figure 11C:
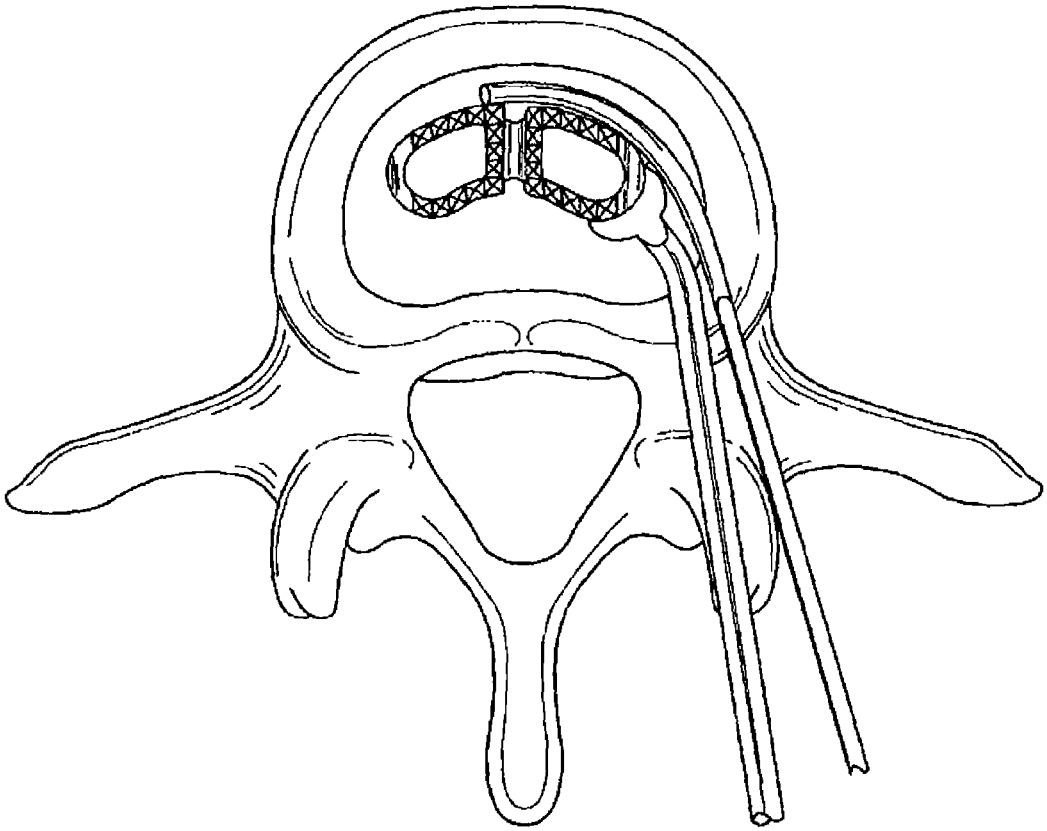

The implant is then introduced into the disc space using the rail as a guide and back-stop for appropriate implant positioning. Using a mallet if necessary, and now referring to FIGS. 11b-11c, the implant is inserted nearly into final positioning.

Figure 11D:
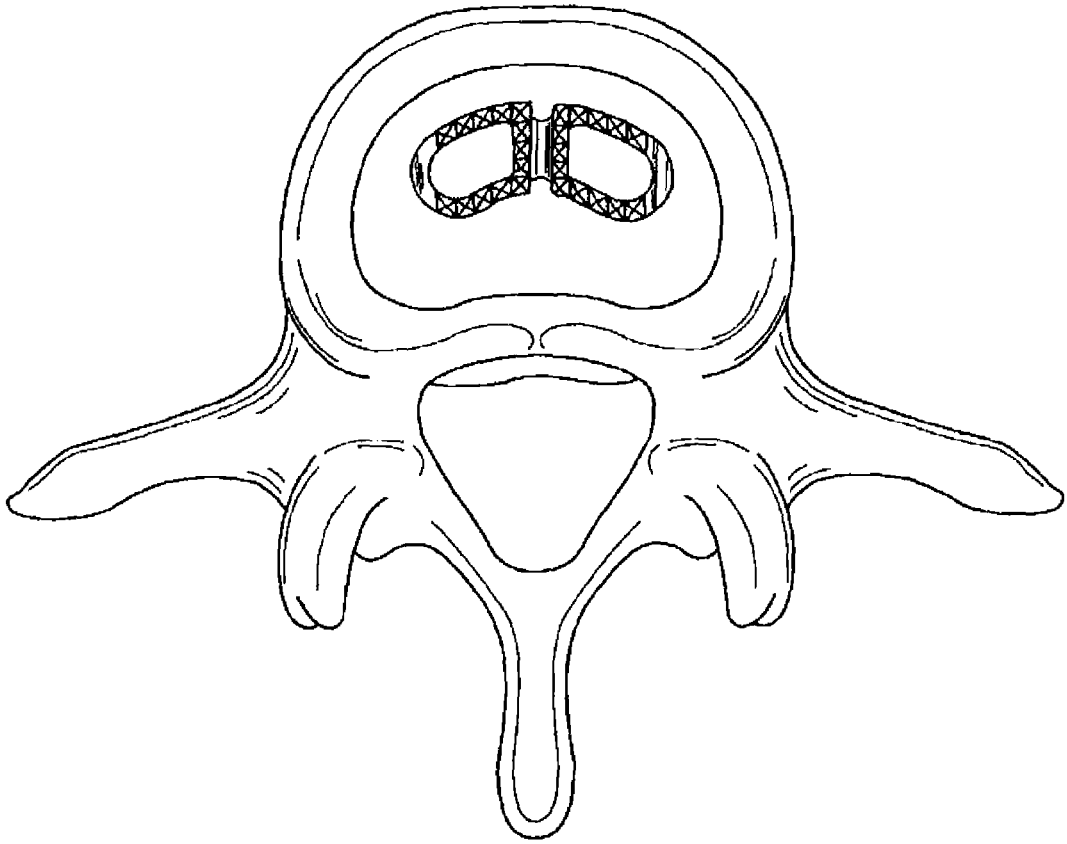

Now referring to FIG. 11d, the inserter is detached from the implant due to anatomical considerations. Straight and/or angled impactors are then used to tamp the cage into final positioning using the rail as the guide.

The final positioning of the implant should be in the anterior portion of the disc space and symmetrically located about the medial-lateral midline of the disc space. This will ensure the most stable construct.

Bone graft or a substitute material may then be packed into the remaining posterior half of the disc space to further promote the interbody fusion.

Should it be necessary to remove the implant at any time during the procedure, a remover may be used.

We claim:

1. An intervertebral fusion device comprising:

a) an anterior wall and a posterior wall defining a width therebetween, wherein the anterior wall has a convex shape and the posterior wall has a concave shape to define a banana shape adapted for non-linear insertion from a posterior side of a spine, b) first and second end walls between the anterior and posterior walls and defining a length therebetween, [and]

c) an upper bearing surface and a lower bearing surface, each having a midline having a recessed ridge running in the anterior-posterior direction and bisecting a right and left side of the device, *and*

[c) a] *d) an* internal planar wall extending transversely from the anterior wall to the posterior wall, and from the upper bearing surface to the lower bearing surface, to define first and second graft chambers, wherein the anterior wall has a middle portion, lateral end portions, each having a maximum height, and the maximum height of the middle portion is greater than the maximum height of the lateral end portions, wherein the width of the device is less than the length of the device, and wherein the length is less than ½ a width of a disc space.

2. The device of claim 1 wherein the length is less than one-third of the width of the disc space.

3. The device of claim 1 wherein a posterior portion of each bearing surface is adapted to bear against an anterior one-third of the disc space.

4. The device of claim 1 being an integral unit.

5. The device of claim 1 wherein the posterior wall has a concave horizontal cross section.

6. The device of claim 1 wherein the anterior wall has a maximum height, the posterior wall has a maximum height, and wherein the maximum height of the anterior wall is greater than the maximum height of the posterior wall.

7. The device of claim 1 wherein the first end wall is a leading end wall adapted for insertion into the disc space, and the leading end wall is tapered.

8. An intervertebral fusion device adapted for non-linear insertion into a disc space comprising:

a) an anterior wall having a convex shape, b) a posterior wall, c) first and second end walls between the anterior and posterior walls, d) an upper bearing surface between the anterior and posterior walls, and having an anterior portion and a posterior portion, [and]

e) a lower bearing surface between the anterior and posterior walls, *and* f) first and second transverse struts extending from the anterior portion of the upper bearing surface to the posterior portion of the upper bearing surface, wherein the anterior wall has a middle portion having a maximum height and lateral end portions each having a maximum height, and the maximum height of the middle portion is greater than the maximum height of the lateral end portions to provide a dome shape, *and* wherein the upper and lower bearing surfaces each have a midline having a recessed ridge running in the anterior-posterior direction and bisecting a right and left side of the device.

9. The device of claim 8 wherein the posterior portion of each bearing surface is adapted to bear against an anterior one-third of the disc space.

10. The device of claim 8 being an integral unit.

11. The device of claim 8 wherein the posterior wall has a concave horizontal cross section.

12. The device of claim 8 adapted for non-linear insertion from a posterior side of the spine.

13. The device of claim 8 wherein the anterior wall has a maximum height, the posterior wall has a maximum height, and wherein the maximum height of the anterior wall is greater than the maximum height of the posterior wall.

14. The device of claim 8 wherein the first end wall is a leading end wall adapted for insertion into the disc space, and the leading end wall is tapered.

15. The device of claim 8 wherein the upper bearing surface comprises at least one upper opening comprising between 30 areal % and 60 areal % of the upper surface.

16. The device of claim 8 wherein the anterior wall has a middle portion, lateral end portions, each having a maximum height, and the maximum height of the middle portion is greater than the maximum height of the lateral end portions.

17. An intervertebral fusion device comprising:

a) an anterior wall having a leading end and a trailing end, b) a posterior wall having a leading end and a trailing end, c) a leading end wall connecting the leading ends of the anterior and posterior walls and having a leading insertion hole, d) a trailing end wall connecting the anterior and posterior walls and having a trailing insertion hole, e) an upper bearing surface between the anterior and posterior walls, and having an anterior portion and a posterior portion, and f) a lower bearing surface between the anterior and posterior walls, wherein the anterior and posterior walls define a centerline therebetween, and wherein the leading and trailing insertion holes are disposed asymmetrically about the centerline, *and* wherein the upper and lower bearing surfaces each have a midline having a recessed ridge running in the anterior-posterior direction and bisecting a right and left side of the device.

18. The device of claim 17 being an integral unit.

19. The device of claim 17 wherein the posterior wall has a concave horizontal cross section.

20. The device of claim 17 adapted for non-linear insertion from a posterior side of a spine.

21. The device of claim 17 wherein the anterior wall has a maximum height, the posterior wall has a maximum height, and wherein the maximum height of the anterior wall is greater than the maximum height of the posterior wall.

22. The device of claim 17 wherein the leading end wall is tapered.

23. The device of claim 17 wherein the anterior wall has a middle portion, lateral end portions, each having a maximum height, and the maximum height of the middle portion is greater than the maximum height of the lateral end portions.

24. An intervertebral fusion device comprising:

a) an anterior wall having a horizontal cross section having a convex shape and a recessed portion, b) a posterior wall, c) first and second end walls between the anterior and posterior walls, d) an upper bearing surface between the anterior and posterior walls having at least one upper opening therethrough adapted to promote bony fusion, wherein the at least one upper opening comprises between 30 areal % and 60 areal % of the upper surface, and e) a lower bearing surface between the anterior and posterior walls having at least one lower opening therethrough adapted to promote bony fusion, wherein the anterior wall has a convex shape and the posterior wall has a concave shape to define a banana shape adapted for non-linear insertion from a posterior side of a spine, and wherein the upper and lower bearing surfaces each have a midline having a recessed ridge running in the anterior-posterior direction and bisecting a right and left side of the device.

25. The device of claim 24 wherein a posterior portion of each bearing surface is adapted to bear against an anterior one-third of a disc space.

26. The device of claim 24 being an integral unit.

27. The device of claim 24 wherein the posterior wall has a concave horizontal cross section.

28. The device of claim 24 adapted for non-linear insertion from a posterior side of a spine.

29. The device of claim 24 wherein the anterior wall has a maximum height, the posterior wall has a maximum height, and wherein the maximum height of the anterior wall is greater than the maximum height of the posterior wall.

30. The device of claim 24 wherein the first end wall is a leading end wall adapted for insertion into a disc space, and the leading end wall is tapered.

31. The device of claim 24 wherein the anterior wall has a middle portion, lateral end portions, each having a maximum height, and the maximum height of the middle portion is greater than the maximum height of the lateral end portions.

32. An intervertebral fusion device comprising:

a) an anterior wall having a convex shape, and a maximum height, b) a posterior wall having a concave shape, c) first and second end walls connecting the anterior and posterior walls, d) an upper bearing surface between the anterior and posterior walls and having a middle portion having a recess, lateral end portions, and at least one upper opening therethrough adapted to promote bony fusion, wherein the at least one upper opening comprises between 30 areal % and 60 areal % of the upper surface, and e) a lower bearing surface having an anterior portion below the anterior wall, a posterior portion below the posterior wall, and at least one lower opening therethrough adapted to promote bony fusion, wherein the anterior wall has a convex shape and the posterior wall has a concave shape to define a banana shape adapted for non-linear insertion from a posterior side of a spine, and wherein the upper and lower bearing surfaces each have a midline having a recessed ridge running in the anterior-posterior direction and bisecting a right and left side of the device.

33. The device of claim 32 wherein a posterior portion of each bearing surface is adapted to bear against an anterior one-third of a disc space.

34. The device of claim 32 being an integral unit.

35. The device of claim 32 wherein the posterior wall has a concave horizontal cross section.

36. The device of claim 32 adapted for non-linear insertion from a posterior side of a spine.

37. The device of claim 32 wherein the anterior wall has a maximum height, the posterior wall has a maximum height, and wherein the maximum height of the anterior wall is greater than the maximum height of the posterior wall.

38. The device of claim 32 wherein the first end wall is a leading end wall adapted for insertion into a disc space, and the leading end wall is tapered.

39. The device of claim 32 wherein the at least one upper opening comprises between 30 areal % and 60 areal % of the upper surface.

40. The device of claim 32 wherein the anterior wall has a middle portion, lateral end portions, each having a maximum height, and the maximum height of the middle portion is greater than the maximum height of the lateral end portions.

*41. An intervertebral fusion device, comprising:*

*a) an anterior wall having a convex shape,*

*b) a posterior wall,*

*c) first and second end walls between the anterior and posterior walls,*

*d) an upper bearing surface between the anterior and posterior walls, and having an anterior portion and a posterior portion, and*

*e) a lower bearing surface between the anterior and posterior walls,*

*wherein the anterior wall has a middle portion having a maximum height and lateral end portions each having a maximum height, and the maximum height of the middle portion is greater than the maximum height of the lateral end portions, and*

*wherein the anterior wall includes a void region that extends at least half way through a width of the device, the void region allowing the device to change shape for insertion into a disc space.*

*42. The device of claim 41, wherein the void region in the anterior wall extends through the upper and lower bearing surfaces.*

*43. The device of claim 41, wherein the void region in the anterior wall allows the device to be articulable to change shape for insertion into a disc space.*

*44. The device of claim 41, wherein the void region in the anterior wall is configured to change in width as the device changes shape for insertion into a disc space.*

*45. The device of claim 41, wherein the posterior wall is continuous without openings formed therein.*

*46. The device of claim 41, wherein the void region extends nearly to the posterior wall.*

*47. The device of claim 41, wherein the posterior wall has a concave horizontal cross-section.*

*48. The device of claim 41, wherein at least one of the upper and lower bearing surfaces has an opening formed therethrough for promoting bony fusion.*

* * * * *